United States Patent
Ebikade et al.

(10) Patent No.: US 12,358,858 B2
(45) Date of Patent: Jul. 15, 2025

(54) LOW-PRESSURE DEPOLYMERIZATION OF LIGNOCELLULOSIC BIOMASS

(71) Applicants: Elvis O. Ebikade, Washington, DC (US); Eric R. Gottlieb, Newark, DE (US); Robert M. O'Dea, Newark, DE (US); Thomas H. Epps, III, Bear, DE (US); Dionisios Vlachos, Newark, DE (US)

(72) Inventors: Elvis O. Ebikade, Washington, DC (US); Eric R. Gottlieb, Newark, DE (US); Robert M. O'Dea, Newark, DE (US); Thomas H. Epps, III, Bear, DE (US); Dionisios Vlachos, Newark, DE (US)

(73) Assignee: University Of Delaware, Newark, DE (US)

( * ) Notice: Subject to any disclaimer, the term of this patent is extended or adjusted under 35 U.S.C. 154(b) by 607 days.

(21) Appl. No.: 17/634,271

(22) PCT Filed: Aug. 14, 2020

(86) PCT No.: PCT/US2020/046384
§ 371 (c)(1),
(2) Date: Feb. 10, 2022

(87) PCT Pub. No.: WO2021/030690
PCT Pub. Date: Feb. 18, 2021

(65) Prior Publication Data
US 2022/0324779 A1    Oct. 13, 2022

Related U.S. Application Data

(60) Provisional application No. 62/887,009, filed on Aug. 15, 2019.

(51) Int. Cl.
*C07C 37/00* (2006.01)
*B01D 3/00* (2006.01)
*B01D 36/00* (2006.01)
*C07C 41/01* (2006.01)
*C07C 41/18* (2006.01)

(52) U.S. Cl.
CPC ............ *C07C 37/004* (2013.01); *B01D 3/009* (2013.01); *B01D 36/00* (2013.01); *C07C 41/01* (2013.01); *C07C 41/18* (2013.01)

(58) Field of Classification Search
CPC .............................. C07C 37/004; C07C 41/01
USPC .......................................................... 568/651
See application file for complete search history.

(56) References Cited

U.S. PATENT DOCUMENTS 9,051,244 B2   6/2015  Dhepe et al.
9,783,474 B2   10/2017 Delgass et al.

2011/0268652 A1    11/2011  Machhammer et al.
2013/0123547 A1*   5/2013   Zhu ........................ C07C 37/01
                                               568/652
2016/0031843 A1*   2/2016   Socha ..................... C07C 215/66
                                               530/502
2017/0152278 A1    6/2017   Samec et al.
2019/0127304 A1    5/2019   Luterbacher et al.
2019/0144690 A1    5/2019   Epps, III et al.

FOREIGN PATENT DOCUMENTS

CN    103508857 A  *  1/2014  ............. C07C 41/01
CN    107935814 A  *  4/2018  ............. B01J 23/002

OTHER PUBLICATIONS

Extended European Search Report for European Application No. 20853018.8, dated Aug. 29, 2023, 11 pages.
Anderson et al., "Reductive Catalytic Fractionation of Corn Stover Lignin," ACS Sustainable Chemistry & Engineering 4, No. 12, Dec. 2016: 6940-6950; Publication date (Web): Sep. 3, 2016.
Bomgardner, M. A., "How perfumers walk the fine line between natural and synthetic", Chem. Eng. News 2019, 97 (16), 9 pages.
Bomgardner, M. A., "The problem with vanilla", Chem. Eng. News 2016, 94 (36), 38-42, 11 pages.
Cheng et al., "Hydrogenolysis of Organosolv Lignin in Ethanol/Isopropanol Media without Added Transition-Metal Catalyst", ACS Sustainable Chem. Eng. 2020, 8 (2), 1023-1030.

(Continued)

*Primary Examiner* — Ana Z Muresan
(74) *Attorney, Agent, or Firm* — BUCHANAN INGERSOLL & ROONEY PC

(57) ABSTRACT

Disclosed herein are systems and methods of depolymerizing a lignin component of a lignin-containing material. The method comprising contacting the lignin-containing material with a solvent and optionally a catalyst at a temperature in the range of 180-300° C. and at a maximum operating pressure of less than 10 barG during the depolymerization of the lignin component of the material and collecting at least one volatile stream comprising one or more depolymerized lignin products. In an embodiment, the step of contacting is carried out in a reactive distillation reactor, and the step of collecting comprises concurrently collecting at least one volatile stream via distillation apparatus connected to the reactive distillation reactor, at least one of the one or more depolymerized lignin products comprises a substituted phenol having the following general formula: (I) wherein $R_1$ is H, methyl, ethyl, n-propyl, propenyl, or allyl, and $R_2$ and $R_3$ are independently selected from H or methoxy group.

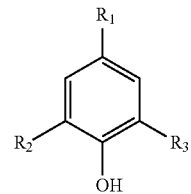

(I)

18 Claims, 13 Drawing Sheets

(56) References Cited

OTHER PUBLICATIONS

Choi et al., "Fast pyrolysis of Kraft lignin—Vapor cracking over various fixed-bed catalysts". J. Anal. Appl. Pyrolysis 2013, 100, 207-212.

Das et al., "Lignin Conversion to Low-Molecular-Weight Aromatics via an Aerobic Oxidation-Hydrolysis Sequence: Comparison of Different Lignin Sources", ACS Sustainable Chem. Eng. 2018, 6 (3), 3367-3374.

Elangovan et al., "From Wood to Tetrahydro-2-benzazepines in Three Waste-Free Steps: Modular Synthesis of Biologically Active Lignin-Derived Scaffolds", ACS Cent. Sci. 2019, 5 (10), 1707-1716.

Fact.MR, "Anti-Microbial Properties of Eugenol to drive the Global Eugenol Market to Reach US$ 754.1 million revenue by 2026 end", https://www.globenewswire.com/news-release/2018/03/07/1417672/0/en/Anti-Microbial-Properties-of-Eugenol-to-drive-the-Global-Eugenol-Market-to-Reach-US-754-1-million-revenue-by-2026-end.html, Mar. 7, 2018, 4 pages.

Gall et al., "Biochemical transformation of lignin for deriving valued commodities from lignocellulose", Curr. Opin. Biotechnol. 2017, 45, 120-126.

Gall et al., "In Vitro Enzymatic Depolymerization of Lignin with Release of Syringyl, Guaiacyl, and Tricin Units", Appl. Environ. Microbiol. 2018. 84 (3), e02076-17.

Kärkäs et al., "Transition-metal catalyzed valorization of lignin: the key to a sustainable carbon-neutral future", Org. Biomol. Chem. 2016, 14 (6), 1853-1914.

Kramárová et al., "Biopolymers as fillers for rubber blends", Polym. Adv. Technol. 2007, 18 (2), 135-140.

Li et al., "An "ideal lignin" facilitates full biomass utilization", Sci. Adv. 2018, 4 (9), eaau2968, 10 pages.

Luo et al., Total Utilization of Miscanthus Biomass, Lignin and Carbohydrates, Using Earth Abundant Nickel Catalyst, ACS Sustainable Chem. Eng. 2016, 4 (4), 2316-2322.

Mottiar et al., "Designer lignins: harnessing the plasticity of lignification", Curr. Opin. Biotechnol. 2016, 37, 190-200.

Parsell et al., "A synergistic biorefinery based on catalytic conversion of lignin prior to cellulose starting from lignocellulosic biomass†", Green Chem. 2015, 17, 1492-1499.

Rahimi et al, "Formic-acid-induced depolymerization of oxidized lignin to aromatics", Nature 2014, 515 (7526), 249-252.

Schutyser et al., "Influence of bio-based solvents on the catalytic reductive fractionation of birch wood", Green Chem., 2015, 13 pages.

(SDA) "Glycerine: an overview", (online) The Soap and Detergent Association. 1990 [retrieved on Mar. 13, 2021). Retrieved from the Internet (URL: https://www.aciscience.org/docs/Glycerine_-_an_overview.pdf ); pp. 1-27.

Shuai et al., "Towards high-yield lignin monomer production", Green Chemistry, 2017, 19 (16), pp. 3752-3758. 2019.

Song et al., "Lignin depolymerization (LDP) in alcohol over nickel-based catalysts via a fragmentation-hydrogenolysis process", Energy & Environment Sciences, downloaded by North Carolina State University on Jan. 18, 2013, published on Jan. 3, 2013, http://pubs.rcs.org, 34 pages.

Sun et al. "Complete lignocellulose conversion with integrated catalyst recycling yielding valuable aromatics and fuels", Nat. Catal. 2018, 1, 82-92.

Toledano et al., "Heterogeneously Catalysed Mild Hydrogenolytic Depolymerisation of Lignin Under Microwave Irradiation with Hydrogen-Donating Solvents", ChemCatChem, 2012 Wiley-VCH Verlag GmbH&Co. KGaA, Weinheim, 10 pages.

Van den Bosch et al., "Integrating lignin valorization and bio-ethanol production: on the role of Ni—Al2O3catalyst pellets during lignin-first fractionation", Green Chem. 2017, 19 (14), 3313-3326.

Van den Bosch et al., "Reductive lignocellulose fractionation into soluble lignin-derived phenolic monomers and dimers and processable carbohydrate pulps", Energy Environ. Sci. 2015, 8 (6), 1748-1763.

Vanholme et al., "Metabolic engineering of novel lignin in biomass crops", New Phytol. 2012, 196 (4), 978-1000.

Vishtal et al., "Challenges in Industrial Applications of Technical Lignins", Bioresources 2011, 6 (3), 3547-3568.

Wang et al., "From Tree to Tape: Direct Synthesis of Pressure Sensitive Adhesives from Depolymerized Raw Lignocellulosic Biomass", ACS Cent. Sci. 2018, 4 (6), 701-708.

International Preliminary Report on Patentability for International Application No. PCT/US2020/046384, dated Feb. 8, 2022, 9 pages.

International Search Report and Written Opinion for International Ap plication No. PCT/US2020/046384, mailed Mar. 22, 2021, 10 pages.

Beckham et al., "Opportunities and challenges in biological lignin valorization", Curr. Opin. Biotechnol. 2016, 42, 40-53.

Carpenter et al., "Biomass feedstocks for renewable fuel production: A review of the impacts of feedstock and pretreatment on the yield and product distribution of fast pyrolysis bio-oils and vapors", Green Chem. 2014, 16 (2), 384-406.

"Filler for Tires", Chem. Eng. News 1957, 35 (22), 28-32.

Galkin et al., "Hydrogen-free catalytic fractionation of woody biomass", ChemSusChem, 2016, 9, 3280-3287.

Galkin et al., "Lignin Valorization through Catalytic Lignocellulose Fractionation: A Fundamental Platform for the Future Biorefinery", ChemSusChem 2016, 9 (13), 1544-1558.

Gandini, A., "The irruption of polymers from renewable resources on the scene of macromolecular science and technology", Green Chem. 2011, 13 (5), 1061-1083.

Klein et al., "Lignin depolymerization over Ni/C catalyst in methanol, a continuation: effect of substrate and catalyst loading", Catal. Sci. Technol., 2015, 5, 3242.

Kumar, T., "Paper jam: Foreign competition and declining demand for paper will continue to plague mills", IBISWorld Industry Report: Paper Mills in the US; 2019, 39 pages.

Laskar et al., "Pathways for biomass-derived lignin to hydrocarbon fuels", Biofuels, Bioprod. Bioref. 2013, 7 (5). 602-626.

Liao et al., "A sustainable wood biorefinery for low-carbon footprint chemicals production", Science 2020, 367, 1385-1390.

Parthasarathi et al., "Theoretical Study of the Remarkably Diverse Linkages in Lignin", J. Phys. Chem. Lett. 2011, 2 (20), 2660-2666.

Rautiainen et al., "Lignin valorization by cobalt-catalyzed fractionation of lignocellulose to yield monophenolic compounds", ChemSusChem 2019, 12 (2), 404-408.

Renders et al., "Reductive catalytic fractionation: state of the art of the lignin-first biorefinery", Curr. Opin. Biotechnol. 2019, 56, 193-201.

Schulyser et al., "Chemicals from lignin: an interplay of lignocellulose fractionation, depolymerisation, and upgrading". Chem. Soc. Rev. 2018, 47 (3), 852-908.

Shuai et al., "Formaldehyde stabilization facilitates lignin monomer production during biomass depolymerization", Science, 2016, 354, 329.

\* cited by examiner

LOW-PRESSURE DEPOLYMERIZATION OF LIGNOCELLULOSIC BIOMASS

CROSS-REFERENCE TO RELATED APPLICATIONS

This application is a national stage application under 35 U.S.C. § 371 of International Application No. PCT/US2020/046384, filed Aug. 14, 2020, which claims priority to U.S. Provisional Patent Application No. 62/887,009 filed Aug. 15, 2019, the entire disclosures of each of these applications being incorporated herein by reference for all purposes.

STATEMENT REGARDING FEDERALLY SPONSORED RESEARCH

This invention was made with government support under Grant No. DE-SC0001004 awarded by the U.S. Department of Energy, Office of Basic Energy Sciences and Grant Nos. CHE-1507010 and CMMI GCR-1934887 awarded by the National Science Foundation. The government has certain rights in the invention.

BACKGROUND OF THE INVENTION

Lignin is a major component of many plants (as much as 25%) and is separated industrially (>70 million tons/year) in the Pulp & Paper industry ($40.5 B, compound annual growth rate –2.6%). Lignin, a major component in lignocellulosic biomass, is the most abundant source of aromatic building blocks in nature, and the depolymerization of lignin is capable of producing value-added small aromatic molecules with great potential as fuel additives and platform chemicals. Unfortunately, the aromatic moieties in lignin are linked by various kinds of robust C—C and C—O bonds, and deconstruction of lignin therefore generates a complex mixture of disparate compounds (monophenols, dimers, and oligomers).

However, the pulp & paper and biorefining industries are struggling due to a decreasing demand for paper and an inability to compete with commodity fuel prices, respectively. Lignin comprises up to 25% of the biomass feedstocks used by these industries and is generally considered a waste product. Upwards of 70 million tons of lignin waste is generated annually, and >98% is burned for energy or landfilled. Lignin's chemical heterogeneity, dark colors, and strong odors currently hinder its commercial value, and, therefore, significant efforts have been made to break down lignin to its constituent aromatic monomers. The fractionation and depolymerization of lignocellulose has been studied extensively, and several processes have been developed, including pyrolytic, catalytic, and enzymatic methods. Reductive catalytic fractionation (RCF) is the most promising approach, producing a selective product mixture with high yields at modest temperatures. However, previously disclosed RCF processes operate under extremely high pressures (>80 bar gauge pressure, barG), requires hazardous reagents (e.g., pressurized $H_2$, methanol), and involves costly product separations.

Hence, there is a need for a novel, cost effective process to depolymerize lignin contained in lignin-containing materials including lignin-rich biomass waste to its constituent monomers at ambient pressure and under less hazardous reagents to produce renewable aromatic chemicals.

SUMMARY OF THE INVENTION

The present invention discloses new processes for depolymerizing a lignin component of a lignin-containing material in the presence of optional hydrogen gas, optional catalyst, and under an operating pressure of less than 10 barG. The reduction in pressure and the elimination of hydrogen are novel innovations that enable facile scale-up and widespread process implementation in addition to reducing capital costs and improving process safety.

Various exemplary aspects of the present invention may be summarized as follows:

In an aspect of the present invention, there is provided a method of depolymerizing a lignin component of a lignin-containing material comprising contacting the lignin-containing material with a solvent and optionally a catalyst at a temperature in the range of 180-300° C. and at a maximum operating pressure of less than 10 barG during the depolymerization of the lignin component of the material; and collecting at least one volatile stream comprising one or more depolymerized lignin products, wherein at least one of the one or more depolymerized lignin products comprises a substituted phenol having the following general formula:

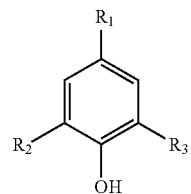

wherein $R_1$ is H, methyl, ethyl, n-propyl, propenyl, or allyl, and $R_2$ and $R_3$ are independently selected from H or methoxy group.

In an embodiment, the step of contacting the lignin-containing material with a solvent and optionally a catalyst comprises contacting in the presence of a hydrogenolysis catalyst comprising Ru, Ni, Raney Ni, Pd, NiPd, NiCu, NiCo, NiRu, RuPd, Fe, Co, Pt, Cu, or mixtures thereof. The catalyst may be supported on a support selected from the group consisting of carbon, alumina, silica, and alumina-silica. In an embodiment, a mass % of the catalyst relative to the lignin component of the lignin-containing material maybe in a range of 0% to 200%.

In an embodiment, the solvent may have a boiling point higher than the reaction temperature. The solvent may be a protic solvent selected from the group consisting of ethylene glycol, glycerin, erythritol, threitol, xylitol, arabitol, ribitol, mannitol, sorbitol, galactitol, fucitol, iditol, inositol, volemitol, monosaccharides, and mixtures thereof.

In an embodiment, the step of contacting the lignin-containing material with a solvent and optionally a catalyst may comprise contacting in the presence of nitrogen, air or argon, without added hydrogen. In another embodiment, the step of contacting the lignin-containing material with a solvent and optionally a catalyst may comprise contacting in the presence of hydrogen at the maximum operating pressure of less than 10 barG.

The step of collecting at least one volatile stream may further comprise extracting one or more depolymerized lignin products from at least one of the collected volatile streams by one of distillation, liquid-liquid extraction, chromatography, or extraction by a base followed by acidification. The one or more depolymerized lignin products may comprise 2-methoxy-4-propylphenol, 2-methoxy-4-ethylphenol, 2-methoxyphenol, 2,6-dimethoxy-4-propylphenol, 2,6-dimethoxy-4-ethylphenol, 2,6-dimethoxyphenol, or mixtures thereof. In an embodiment, at least one volatile stream may comprise one or more non-phenolic compounds. The non-phenolic compounds may comprise substituted furans, substituted methoxybenzenes, substituted cyclopentanones, substituted cyclopentenones, dioxalanes, solketal, and mixtures thereof.

In an embodiment, the lignin-containing material may comprise untreated lignocellulosic biomass selected from woods, grasses, cereal crops and waste; partially treated lignocellulosic biomass, an isolated lignin, or mixtures thereof. In another embodiment, the lignin-containing material may comprise oak, alder, chestnut, ash, aspen, balsa, beech, birch, boxwood, walnut, laurel, camphor, chestnut, cherry, dogwood, elm, *eucalyptus*, pear, hickory, ironwood, maple, olive, poplar, *sassafras*, rosewood, coconut, locust, willow trees, *miscanthus*, switchgrass, bamboo, straw, barley, millet, wheat, corn stover, sugarcane bagasse, nutshells, olive seeds, tomato peels, brewers' spent grain (BSG), seeds, lignin-containing yard waste, lignin-containing municipal solid waste, lignin residue generated by cellulosic biorefinery and paper pulping industries, and mixtures thereof.

In an aspect of the method, the step of contacting the lignin-containing material with a solvent and optionally a catalyst may be carried out in a reactive distillation reactor, and the step of collecting at least one volatile stream may comprise concurrently collecting at least one volatile stream via distillation apparatus connected to the reactive distillation reactor.

In another aspect of the method, the step of contacting the lignin-containing material with a solvent and optionally a catalyst may be carried out in a closed cell reactor, and the subsequent step of collecting at least one volatile stream may comprise collecting at least one volatile stream via distillation apparatus connected to the closed cell reactor, after the step of contacting the lignin-containing material with a solvent and optionally a catalyst.

In an aspect, there is provided a method comprising providing a composition comprising one or more depolymerized lignin products, a solvent, and optionally one or more of partially depolymerized lignin, residual cellulose/hemicellulose and other non-lignin feedstock components, wherein the solvent has lower volatility than one or more of the depolymerized lignin products; and distilling one or more depolymerized lignin products from the composition, wherein at least one of the one or more depolymerized lignin products comprises a substituted phenol having the following general formula:

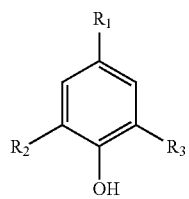

wherein $R_1$ is H, methyl, ethyl, n-propyl, propenyl, allyl, or formyl, and $R_2$ and $R_3$ are independently selected from H or methoxy group. The solvent having lower volatility than one or more of the depolymerized lignin products may be selected from the group consisting of ethylene glycol, glycerin, erythritol, threitol, xylitol, arabitol, ribitol, mannitol, sorbitol, galactitol, fucitol, iditol, inositol, volemitol, monosaccharides, and mixtures thereof.

In yet another aspect, there is provided a system for depolymerizing a lignin component of a lignin-containing material comprising a reactive distillation reactor configured to receive lignin-containing material and a solvent and to operate at a temperature in the range of 180-300° C. and at a maximum operating pressure of less than 10 barG; and a distillation apparatus connected to the reactive distillation reactor, and configured for concurrent collection of at least one volatile stream produced by contact of the lignin-containing material with the solvent in the reactive distillation reactor, wherein at least one volatile stream comprises one or more depolymerized lignin products comprising a substituted phenol having the following general formula:

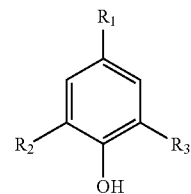

wherein $R_1$ is H, methyl, ethyl, n-propyl, propenyl, or allyl, and $R_2$ and $R_3$ are independently selected from H or methoxy group. The system may also comprise a filtration apparatus connected to the reactive distillation reactor, wherein the filtration apparatus is configured to receive contents of the reactive distillation reactor and to separate the contents into a stream comprising lignin oligomers and solvent from insoluble solids. The system may further comprise a solvent recycling apparatus configured to receive the stream comprising lignin oligomers and solvent and to separate the solvent and recycle the solvent back to the reactive distillation reactor.

In another aspect, there is a system for depolymerizing a lignin component of a lignin-containing material comprising a closed cell reactor configured to receive lignin-containing material and a solvent and to operate at a temperature in the range of 180-300° C. and at a maximum operating pressure of less than 10 barG and a filtration apparatus connected to the closed cell reactor, wherein the filtration apparatus is configured to receive contents of the closed cell reactor and to separate the contents into a stream comprising depolymerized lignin products and solvent, and insoluble solids, wherein the depolymerized lignin products are produced by contact of the lignin-containing material with the solvent in the closed cell reactor, wherein the depolymerized lignin products comprises a substituted phenol having the following general formula:

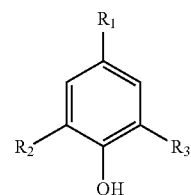

wherein $R_1$ is H, methyl, ethyl, n-propyl, propenyl, or allyl, and $R_2$ and $R_3$ are independently selected from H or methoxy group. The system may further comprise a distillation apparatus connected to the filtration apparatus, and configured for collection of the stream comprising depolymerized lignin products and solvent and separation of the stream into one or more volatile streams comprising the depolymerized lignin products and a solvent stream. The system may also comprise a solvent recycling apparatus connected to the distillation apparatus, and configured to receive the solvent stream and to recycle the solvent back to the closed cell reactor.

DETAILED DESCRIPTION OF THE INVENTION

Figure 1:
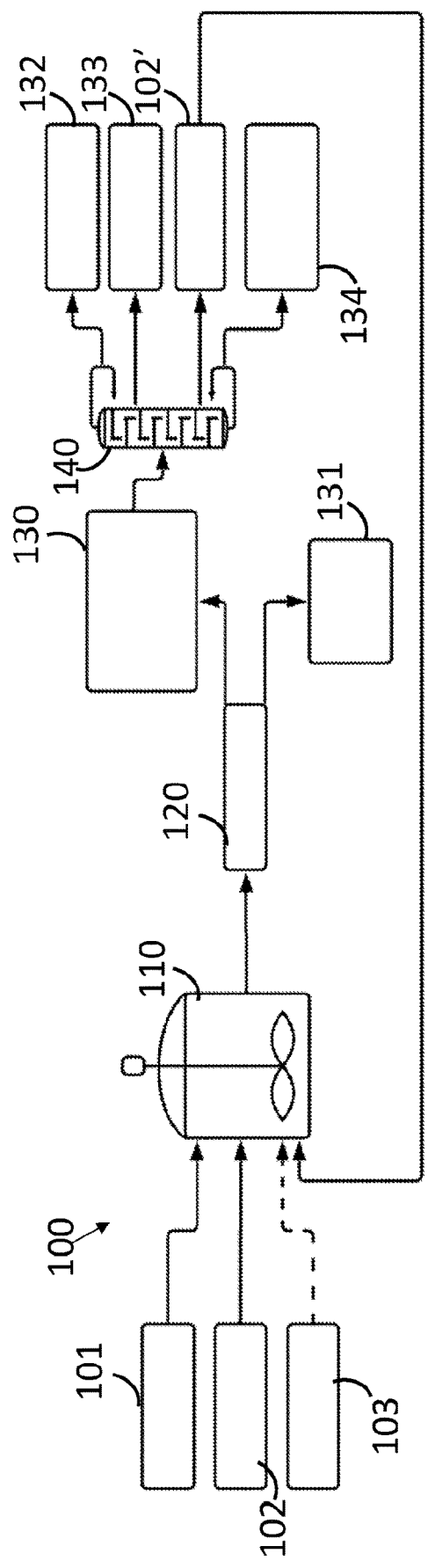
FIG. 1 displays an exemplary process flow diagram showing a method of depolymerizing a lignin component of a lignin-containing material in a closed system, according to embodiments of the present invention.

The present invention discloses novel processes and systems that facilitates the depolymerization of lignin-containing material.

In an aspect, there is provided a method of depolymerizing a lignin component of a lignin-containing material comprising contacting the lignin-containing material with a solvent and optionally a catalyst at a temperature in the range of 180-300° C. and at a maximum operating pressure of less than 10 barG during the depolymerization of the lignin component of the material and collecting at least one volatile stream comprising one or more depolymerized lignin products, wherein at least one of the one or more depolymerized lignin products comprises a substituted phenol having the following general formula:

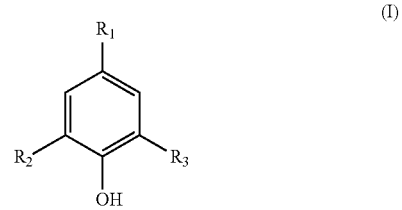

(I)

wherein $R_1$ is H, methyl, ethyl, n-propyl, propenyl, or allyl, and $R_2$ and $R_3$ are independently selected from H or methoxy group.

In some embodiments, the one or more depolymerized lignin products may comprise one or more substituted phenolic compounds and one or more non-phenolic compounds. The phenolic compounds have at least one phenolic hydroxyl group, and have a structure corresponding to formula (I), as shown above. In an embodiment, the one or more depolymerized lignin products may include 2-methoxy-4-propylphenol (4-propylguaiacol), 2-methoxy-4-ethylphenol (4-ethylguaiacol), 2-methoxyphenol (guaiacol), 2,6-dimethoxy-4-propylphenol (4-propylsyringol), 2,6-dimethoxy-4-ethylphenol (4-ethylsyringol), 2,6-dimethoxyphenol (syringol), or mixtures thereof. In one embodiment, $R_1$ is n-propyl, $R_2$ is H and $R_3$ is methoxy group, and the resulting depolymerized lignin product comprises a bio-derived propyl-Guaiacol (pG). In another embodiment, $R_1$ is n-propyl, each of $R_2$ and $R_3$ is methoxy group, and the resulting depolymerized lignin product comprises a bio-derived propyl-Syringol (pS). In another embodiment, the one or more depolymerized lignin products comprises a mixture of bio-derived pG and bio-derived pS. In another embodiment, the one or more depolymerized lignin products comprises a mixture of bio-derived guaiacol, bio-derived pG, and bio-derived pS. In another embodiment, the one or more depolymerized lignin products comprises a mixture of bio-derived syringol, bio-derived pG, and bio-derived pS. In yet another embodiment, $R_1$ is n-ethyl, $R_2$ is H and $R_3$ is methoxy group, and the resulting depolymerized lignin product comprises a bio-derived ethyl-Guaiacol (eG). In another embodiment, $R_1$ is ethyl, each of $R_2$ and $R_3$ is methoxy group, and the resulting depolymerized lignin product comprises a bio-derived ethyl-Syringol (eS). In another embodiment, the one or more depolymerized lignin products comprises a mixture of bio-derived eG and bio-derived eS. In an embodiment, the one or more depolymerized lignin products comprises a mixture of bio-derived guaiacol, bio-derived eG, and bio-derived eS. In an embodiment, the one or more depolymerized lignin products comprises a mixture of bio-derived syringol, bio-derived eG, and bio-derived eS.

The non-phenolic compounds present in the one or more depolymerized lignin products may include, but are not limited to one or more of:

(i) substituted furans, as shown by formula (II):

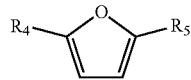

(II)

where $R_4$ is H, methyl, hydroxyl and $R_5$ is H or carbonyl, (ii) one or more of substituted methoxybenzenes, as shown below by formula (III):

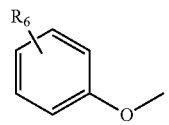

(III)

where $R_6$ is H, methyl or methoxy.

(iii) substituted cyclopentanones, as shown below by formula (IV):

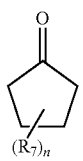

(IV)

where $R_7$ is independently H or methyl and n=1-3.

(iv) substituted cyclopentenones, as shown below by formula (V)

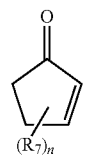

(V)

where $R_7$ is independently H or methyl and n=1-3.

(v) dioxolane, as shown below by formula (VI):

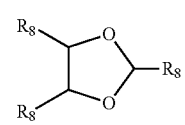

(VI)

where each $R_8$ is independently selected from methyl, hydroxyl, or methoxyl group.

(vi) solketal, as shown below by formula (VII):

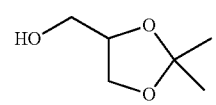

(VII)

The relative amounts of the one or more phenolic compounds and the one or more non-phenolic compounds depend on the lignin-containing material feedstock and depolymerisation reaction conditions, including, but not limited to catalyst, temperature, presence or absence of hydrogen, and the solvent.

In an embodiment, the lignin-containing material is a lignocellulosic biomass or a mixture containing lignocellulosic biomass. Suitable examples of lignocellulosic biomass include, for example and without limitation, woods (e.g., oak, alder, chestnut, ash, aspen, balsa, beech, birch, boxwood, walnut, laurel, camphor, chestnut, cherry, dogwood, elm, *eucalyptus*, pear, hickory, ironwood, maple, olive, poplar, *sassafras*, rosewood, coconut, locust, and willow trees), as well as, but not limited to, grasses (e.g., *miscanthus*, switchgrass, bamboo, straw), cereal crops (e.g., barley, millet, wheat), as well as, but not limited to, wastes (e.g. agricultural residues (e.g., corn stover, sugarcane bagasse), lignin-containing food wastes (e.g., nutshells, olive seeds, tomato peels, brewers' spent grain (BSG), and seeds), lignin-containing yard waste, lignin-containing municipal solid waste, lignin residue generated by cellulosic biorefinery and paper pulping industries, and mixtures thereof.

In another embodiment, the lignin-containing material is any lignocellulosic biomass or any mixture containing lignocellulosic biomass which has been treated or partly treated to remove one or more non-lignin component partly or entirely from the lignocellulosic biomass. Suitable examples of treatment or partial treatment of any lignocellulosic biomass or any mixture containing any lignocellulosic biomass include, for example and without limitation, solvent extraction, thermal treatment, extractive removal, partial or total hydrolysis, protein extraction, pulping, or combinations thereof.

In yet another embodiment, the lignin-containing material is an isolated lignin, which may be isolated from any lignocellulosic biomass or any mixture containing lignocellulosic biomass or any treated or partially treated lignocellulosic biomass or any treated or partly treated mixture containing lignocellulosic biomass. Suitable examples of isolated lignin include, but are not limited to, Kraft lignin, organosolv lignin, soda lignin, thermomechanical pulping lignin, sulfonated lignin, and biorefinery lignin.

In an embodiment, the step of contacting the lignin-containing material with a solvent and optionally a catalyst comprises contacting in the presence of a hydrogenolysis catalyst. In another embodiment, the step of contacting the lignin-containing material with a solvent and optionally a catalyst comprises contacting in an absence of a hydrogenolysis catalyst, i.e. hydrogenolysis catalyst is not added to the reaction mixture comprising lignin-containing material and the solvent. Any suitable hydrogenolysis catalyst may be used, including, but not limited to Ru, Ni, Raney Ni, Pd, NiPd, NiCu, NiCo, NiRu, RuPd, Fe, Co, Pt, Cu, or mixtures thereof. In an embodiment, the catalyst may be unsupported, such as Raney Nickel. In another embodiment, the catalyst is support on a support selected from the group consisting of carbon, alumina, silica, and alumina-silica.

Any suitable amount of catalyst may be used, such as a mass % of catalyst relative to the lignin component of the lignin-containing material in a range of 0% to 200%, or 0% to 100%, or 0% to 50%, or 0% to 25%.

Additionally, any suitable solvent may be used. In an embodiment, the solvent has a boiling point higher than the reaction temperature. Suitable protic solvents include, but are not limited to ethylene glycol, glycerin, erythritol, threitol, xylitol, arabitol, ribitol, mannitol, sorbitol, galactitol, fucitol, iditol, inositol, volemitol, other sugar alcohols, monosaccharides, and mixtures thereof. In an embodiment of the method, the step of contacting the lignin-containing material with a solvent and optionally a catalyst does not comprise contacting with added methanol as a solvent. However, methanol may be present in the protic solvent to be contacted with the lignin-containing material as an inevitable impurity. In an embodiment, the volatility of the solvent is less than that of the depolymerized lignin products. In another embodiment, the boiling point of the solvent is higher than the reaction temperature, which allows the process to operate at much lower pressures, such as at a maximum operating pressure of 10 barG or less.

Any suitable amount of solvent may be added. In an embodiment, the solvent to biomass ratio by volume:mass ratio (e.g., 20 mL of solvent per 1 g of lignin containing material) is in the range of 5:1, to 50:1 or 10:1 to 20:1.

In an embodiment of the method, the step of contacting the lignin-containing material with a solvent may include contacting in the presence of nitrogen, air, or argon, without added hydrogen. In another embodiment of the method, the step of contacting the lignin-containing material with a solvent and optionally a catalyst may include contacting in the presence of hydrogen at the maximum operating pressure of less than 10 barG, or less than 7 barG, or less than 5 barG, or less than 2 barG and greater than −1 barG or greater than 0 barG, or greater than 1 barG. In an embodiment, hydrogen is added at a pressure of, less than the maximum operating pressure, such as in the range of 1-8 barG or 1-6 barG, or 1-4 barG, thereby to ensure that the maximum operating pressure during the course of the reaction remains less than 10 barG.

In an embodiment of the method, the step of contacting may be carried out for any suitable time and temperature. Suitable amount of time for contacting the lignin-containing material with a solvent and optionally a catalyst may be in a range of 30 minutes to 20 hours, or 2 hours to 12 hours, or 4 hours to 10 hours. Suitable temperature for the step of contacting the lignin-containing material with a solvent and optionally a catalyst may be in a range of 180 to 300° C., or 200 to 290° C., or 230 to 280° C., or 240 to 270° C.

In another embodiment of the method, the step of collecting at least one volatile stream may further include extracting one or more depolymerized lignin products from at least one of the collected volatile streams by one of distillation, liquid-liquid extraction, chromatography, or extraction by a base followed by acidification.

The step of contacting and the step of collecting may be done in a batch, continuous or semi-continuous manner.

In an aspect of the invention, the step of contacting the lignin-containing material with a solvent and optionally a catalyst is carried out in a closed cell reactor, and wherein the step of collecting at least one volatile stream comprises collecting at least one volatile stream via distillation apparatus connected to the closed cell reactor, after the step of contacting the lignin-containing material with a solvent and optionally a catalyst. The distillation apparatus may be connected to the closed cell reactor either directly or indirectly such as with a filtration apparatus in between the reactor and the distillation unit.

The step of contacting the lignin-containing material with a solvent and optionally a catalyst and the step of collecting at least one volatile stream may be done in a batch, continuous or semi-continuous manner. The step of collecting at least one volatile stream is said to be subsequent to the step of contacting the lignin-containing material with a solvent and optionally a catalyst when the distillation apparatus is placed after the closed cell system, independent of the steps being performed in a batch, continuous or semi-continuous manner.

FIG. 1 displays an exemplary process flow diagram 100 showing a method of depolymerizing a lignin component of a lignin-containing material in a closed system. As shown in FIG. 1, the method 100 comprises contacting the lignin-containing material 101 with a solvent 102 and an optional catalyst 103 being carried out in a closed cell reactor 110 at a temperature in the range of 180-300° C. at a maximum operating pressure in the range of vacuum (−1 to 0 barG) to 10 barG for any suitable amount of time, such for 30 minutes to 20 hours or 1 hour to 15 hours or 3 hours to 12 hours. After the end of the suitable amount of reaction time, the reaction mixture comprising the lignin-containing material 101, the solvent 102 and the optional catalyst 103, undergoes filtration 120 to separate a mixture 130 from insoluble solids 131. The mixture 130 may comprise one or more depolymerized lignin products 134, partially depolymerized lignin products 136, volatile byproducts 132, and the solvent 102'. The method 100 may further comprise subsequently carrying out distillation 140 after filtration 120, using the mixture 130 and collecting one or more streams, such that at least one stream is a volatile stream comprising one or more depolymerized lignin products 132 and optionally a stream of volatile byproducts 132. In another embodiment, the solvent 102' and the partially depolymerized lignin products 134 may be collected as separate streams and the solvent 102' may be recycled back to the reactor 110.

In another aspect of the invention, the step of contacting the lignin-containing material with a solvent and optionally a catalyst is carried out in a reactive distillation reactor, and wherein the step of collecting at least one volatile stream comprises collecting at least one volatile stream via distillation apparatus connected to the reactive distillation reactor.

The step of contacting the lignin-containing material with a solvent and optionally a catalyst and the step of collecting at least one volatile stream in a reactive distillation reactor may be done in a batch, continuous or semi-continuous manner. The step of collecting at least one volatile stream is said to be concurrent to the step of contacting the lignin-containing material with a solvent and optionally a catalyst when the distillation apparatus is connected to the reactive distillation reactor, independent of the steps being performed in a batch, continuous or semi-continuous manner.

Figure 2:
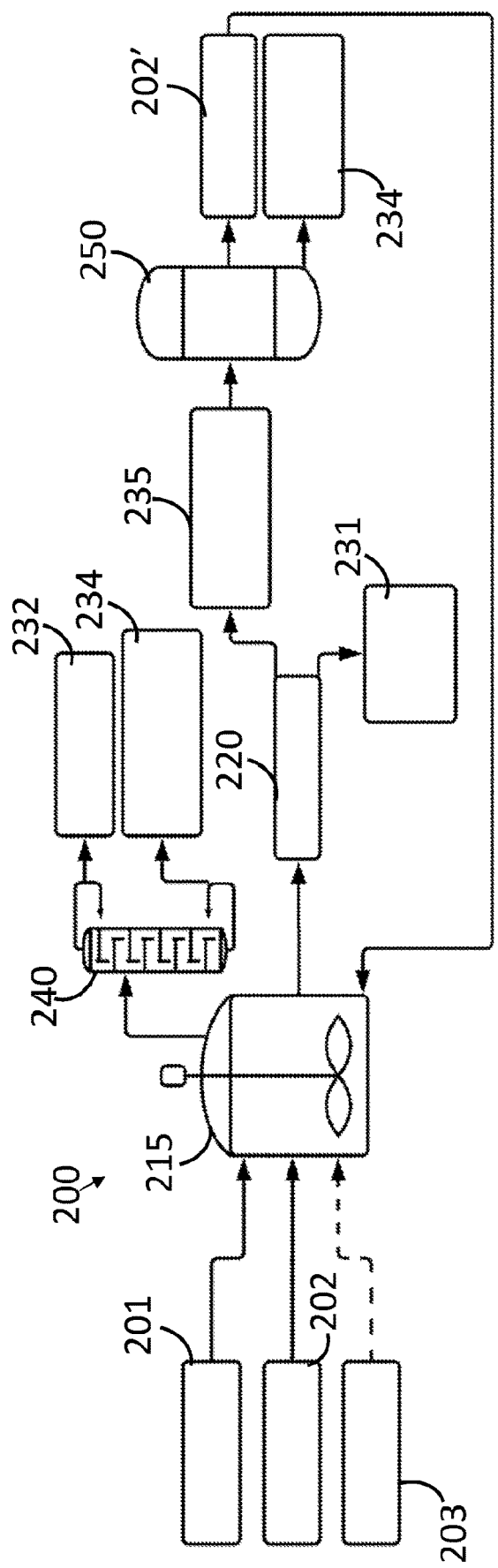
FIG. 2 displays an exemplary process flow diagram showing a method of depolymerizing a lignin component of a lignin-containing material using a reactive distillation system, according to embodiments of the present invention.

FIG. 2 displays an exemplary process flow diagram 200 showing a method of depolymerizing a lignin component of a lignin-containing material in a reactive distillation system. As shown in FIG. 2, the method 200 comprises contacting the lignin-containing material 201 with a solvent 202 and an optional catalyst 203 is carried out in a reactive distillation reactor 215 at a temperature in the range of 180-300° C. at a maximum operating pressure in the range of vacuum (−1 to 0 barG) to 10 barG or 5 to 10 barG or 0 to 5 barG and concurrently collecting one or more volatile streams such as a volatile stream comprising one or more depolymerized lignin products 234 and another volatile stream comprising volatile byproducts 232 (i.e., non-aromatic compounds) via a distillation apparatus 240 connected to the reactive distillation reactor 210 and configured for concurrent collection of at least one volatile stream produced by contact of the lignin-containing material with the solvent in the reactive distillation reactor 210. After the end of a suitable amount of reaction time, the reaction mixture, comprising one or more partially depolymerized lignin products, insoluble solids, and a solvent, from the reactive distillation reactor 215 may undergo filtration 220 to separate the mixture into a stream 235 comprising one or more partially depolymerized lignin products in a solvent, from insoluble solids 231. The method 200 may further comprise a step 250 of recycling solvent from the stream 235 and adding the recovered solvent 202' back to the reactive distillation reactor 210. Any suitable method may be used to separate the solvent from the stream 235, including, but not limited to, distillation, membrane filtration, or chromatography.

In yet another aspect of the invention, there is provided a method comprising the steps of providing a composition comprising one or more depolymerized lignin products from a lignin-containing material, a solvent, and optionally one or more of partially depolymerized lignin, residual cellulose/hemicellulose and other non-lignin feedstock components, wherein the solvent has lower volatility than one or more of the depolymerized lignin products; and distilling one or more depolymerized lignin products from the composition, wherein at least one of the one or more depolymerized lignin, as disclosed hereinabove. In other words, the solvent has higher boiling point as compared to the one or more of the depolymerized lignin products. In an embodiment, at least one of the one or more depolymerized lignin products comprises a substituted phenol having the following general formula:

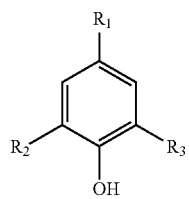

wherein $R_1$ is H, methyl, ethyl, n-propyl, propenyl, allyl, or formyl, and $R_2$ and $R_3$ are independently selected from H or methoxy group.

Any suitable solvent having a boiling higher than the reaction temperature may be used. In an embodiment, the solvent is selected from the group consisting of ethylene glycol, glycerin, erythritol, threitol, xylitol, arabitol, ribitol, mannitol, sorbitol, galactitol, fucitol, iditol, inositol, volemitol, monosaccharides, and mixtures thereof.

In another aspect of the invention, there is provided a system for depolymerizing a lignin component of a lignin-containing material, using a process as summarized in FIG. 2. The system comprising a reactive distillation reactor configured to receive lignin-containing material and a solvent and to operate at a temperature in the range of 180-300° C. and at a maximum operating pressure of less than 10 barG. The system also comprises a distillation apparatus connected to the reactive distillation reactor, and configured for concurrent collection of at least one volatile stream produced by contact of the lignin-containing material with the solvent in the reactive distillation reactor, wherein at least one volatile stream comprises one or more depolymerized lignin products comprising a substituted phenol having the following general formula:

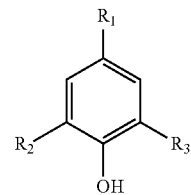

wherein $R_1$ is H, methyl, ethyl, n-propyl, propenyl, or allyl, and $R_2$ and $R_3$ are independently selected from H or methoxy group.

In an embodiment, the system further comprises a filtration apparatus connected to the reactive distillation reactor, wherein the filtration apparatus is configured to receive contents of the reactive distillation reactor and to separate the contents into a stream comprising lignin oligomers and solvent from insoluble solids.

In another embodiment, the system may further comprise a solvent recycling apparatus configured to receive the stream comprising lignin oligomers and solvent and to separate the solvent and recycle back to the reactive distillation reactor.

In yet another aspect of the invention, there is provided a system for depolymerizing a lignin component of a lignin-containing material using a method as summarized in FIG. 1. The system comprises a closed cell reactor configured to receive lignin-containing material and a solvent and to operate at a temperature in the range of 180-300° C. and at a maximum operating pressure of less than 10 barG and a filtration apparatus connected to the closed cell reactor, wherein the filtration apparatus is configured to receive contents of the closed cell reactor and to separate the contents into a stream comprising depolymerized lignin products and solvent, and insoluble solids, wherein the depolymerized lignin products are produced by contact of the lignin-containing material with the solvent in the closed cell reactor, wherein the depolymerized lignin products comprises a substituted phenol having the following general formula:

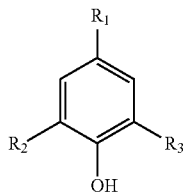

wherein $R_1$ is H, methyl, ethyl, n-propyl, propenyl, or allyl, and $R_2$ and $R_3$ are independently selected from H or methoxy group.

In an embodiment, the system may further comprise a distillation apparatus connected to the filtration apparatus, and configured for collection of the stream comprising depolymerized lignin products and solvent and separation of the stream into one or more volatile streams comprising the depolymerized lignin products and a solvent stream. In another embodiment, the system may also comprise a solvent recycling apparatus connected to the distillation apparatus, and configured to receive the solvent stream recycle the solvent back to the closed cell reactor.

ASPECTS OF THE INVENTION

Certain illustrative, non-limiting aspects of the invention may be summarized as follows:

Aspect 1. A method of depolymerizing a lignin component of a lignin-containing material comprising:
(i) contacting the lignin-containing material with a solvent and optionally a catalyst at a temperature in the range of 180-300° C. and at a maximum operating pressure of less than 10 barG during the depolymerization of the lignin component of the material; and
(ii) collecting at least one volatile stream comprising one or more depolymerized lignin products, wherein at least one of the one or more depolymerized lignin products comprises a substituted phenol having the following general formula:

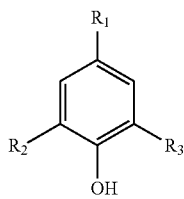

wherein $R_1$ is H, methyl, ethyl, n-propyl, propenyl, or allyl, and $R_2$ and $R_3$ are independently selected from H or methoxy group.

Aspect 2. The method according to Aspect 1, wherein the step of contacting the lignin-containing material with a solvent and optionally a catalyst comprises contacting in the presence of a hydrogenolysis catalyst.

Aspect 3. The method according to Aspect 2, wherein the catalyst comprises Ru, Ni, Raney Ni, Pd, NiPd, NiCu, NiCo, NiRu, RuPd, Fe, Co, Pt, Cu, or mixtures thereof.

Aspect 4. The method according to Aspect 3, wherein the catalyst is supported on a support selected from the group consisting of carbon, alumina, silica, and alumina-silica.

Aspect 5. The method according to any one of the Aspects 2-4, wherein a mass % of catalyst relative to the lignin component of the lignin-containing material is in a range of 0% to 200%.

Aspect 6. The method according to any one of the Aspects 1-5, wherein the solvent has a boiling point higher than the reaction temperature.

Aspect 7. The method according to any one of the Aspects 1-6, wherein the solvent is a protic solvent selected from the group consisting of ethylene glycol, glycerin, erythritol, threitol, xylitol, arabitol, ribitol, mannitol, sorbitol, galactitol, fucitol, iditol, inositol, volemitol, monosaccharides, and mixtures thereof.

Aspect 8. The method according to any one of the Aspects 1-7, wherein the step of contacting the lignin-containing material with a solvent and optionally a catalyst comprises contacting in the presence of nitrogen, air or argon, without added hydrogen.

Aspect 9. The method according to any one of the Aspects 1-7, wherein the step of contacting the lignin-containing material with a solvent and optionally a catalyst comprises contacting in the presence of hydrogen at the maximum operating pressure of less than 10 barG.

Aspect 10. The method according to any one of the Aspects 1-9, wherein the step of collecting at least one volatile stream further comprises extracting one or more depolymerized lignin products from at least one of the collected volatile streams by one of distillation, liquid-liquid extraction, chromatography, or extraction by a base followed by acidification.

Aspect 11. The method according to any one of the Aspects 1-10, wherein the volatile depolymerized lignin products comprise 2-methoxy-4-propylphenol, 2-methoxy-4-ethylphenol, 2-methoxyphenol, 2,6-dimethoxy-4-propylphenol, 2,6-dimethoxy-4-ethylphenol, 2,6-dimethoxyphenol, or mixtures thereof.

Aspect 12. The method according to any one of the Aspects 1-11, wherein at least one volatile stream comprises one or more non-phenolic compounds.

Aspect 13. The method according to Aspect 12, wherein the non-phenolic compounds comprise substituted furans, substituted methoxybenzenes, substituted cyclopentanones, substituted cyclopentenones, dioxalanes, solketal, and mixtures thereof.

Aspect 14. The method according to any one of the Aspects 1-13, wherein the lignin-containing material comprises untreated lignocellulosic biomass selected from woods, grasses, cereal crops and waste; partially treated lignocellulosic biomass, an isolated lignin, or mixtures thereof.

Aspect 15. The method according to any one of the Aspects 1-13, wherein the lignin-containing material comprises oak, alder, chestnut, ash, aspen, balsa, beech, birch, boxwood, walnut, laurel, camphor, chestnut, cherry, dogwood, elm, *eucalyptus*, pear, hickory, ironwood, maple, olive, poplar, *sassafras*, rosewood, coconut, locust, willow trees, *miscanthus*, switchgrass, bamboo, straw, barley, millet, wheat, corn stover, sugarcane bagasse, nutshells, olive seeds, tomato peels, brewers' spent grain (BSG), seeds, lignin-containing yard waste, lignin-containing municipal solid waste, lignin residue generated by cellulosic biorefinery and paper pulping industries, and mixtures thereof.

Aspect 16. The method according to any one of the Aspects 1-15, wherein the step of contacting the lignin-containing material with a solvent and optionally a catalyst is carried out in a reactive distillation reactor, and wherein the step of collecting at least one volatile stream comprises concurrently collecting at least one volatile stream via distillation apparatus connected to the reactive distillation reactor.

Aspect 17. The method according to any one of the Aspects 1-17, wherein the step of contacting the lignin-containing material with a solvent and optionally a catalyst is carried out in a closed cell reactor, and wherein the subsequent step of collecting at least one volatile stream comprises collecting at least one volatile stream via distillation apparatus connected to the closed cell reactor, after the step of contacting the lignin-containing material with a solvent and optionally a catalyst.

Aspect 18. A method comprising:
(i) providing a composition comprising one or more depolymerized lignin products, a solvent, and optionally one or more of partially depolymerized lignin, residual cellulose/hemicellulose and other non-lignin feedstock components, wherein the solvent has lower volatility than one or more of the depolymerized lignin products; and
(ii) distilling one or more depolymerized lignin products from the composition, wherein at least one of the one or more depolymerized lignin products comprises a substituted phenol having the following general formula:

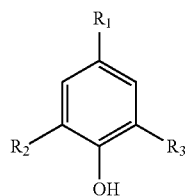

wherein $R_1$ is H, methyl, ethyl, n-propyl, propenyl, allyl, or formyl, and $R_2$ and $R_3$ are independently selected from H or methoxy group.

Aspect 19. The method of Aspect 18, wherein the solvent is selected from the group consisting of ethylene glycol, glycerin, erythritol, threitol, xylitol, arabitol, ribitol, mannitol, sorbitol, galactitol, fucitol, iditol, inositol, volemitol, monosaccharides, and mixtures thereof.

Aspect 20. A system for depolymerizing a lignin component of a lignin-containing material comprising:
(i) a reactive distillation reactor configured to receive lignin-containing material and a solvent and to operate at a temperature in the range of 180-300° C. and at a maximum operating pressure of less than 10 barG; and
(ii) a distillation apparatus connected to the reactive distillation reactor, and configured for concurrent collection of at least one volatile stream produced by contact of the lignin-containing material with the solvent in the reactive distillation reactor,
wherein at least one volatile stream comprises one or more depolymerized lignin products comprising a substituted phenol having the following general formula:

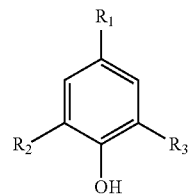

wherein $R_1$ is H, methyl, ethyl, n-propyl, propenyl, or allyl, and $R_2$ and $R_3$ are independently selected from H or methoxy group Aspect 21. The system of Aspect 20 further comprising a filtration apparatus connected to the reactive distillation reactor, wherein the filtration apparatus is configured to receive contents of the reactive distillation reactor and to separate the contents into a stream comprising lignin oligomers and solvent from insoluble solids.

Aspect 22. The system of Aspect 20 further comprising a solvent recycling apparatus configured to receive the stream comprising lignin oligomers and solvent and to separate the solvent and recycle back to the reactive distillation reactor.

Aspect 23. A system for depolymerizing a lignin component of a lignin-containing material comprising:
(i) a closed cell reactor configured to receive lignin-containing material and a solvent and to operate at a temperature in the range of 180-300° C. and at a maximum operating pressure of less than 10 barG; and
(ii) a filtration apparatus connected to the closed cell reactor, wherein the filtration apparatus is configured to receive contents of the closed cell reactor and to separate the contents into a stream comprising depolymerized lignin products and solvent, and insoluble solids, wherein the depolymerized lignin products are produced by contact of the lignin-containing material with the solvent in the closed cell reactor,
wherein the depolymerized lignin products comprises a substituted phenol having the following general formula:

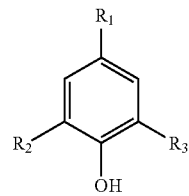

wherein $R_1$ is H, methyl, ethyl, n-propyl, propenyl, or allyl, and $R_2$ and $R_3$ are independently selected from H or methoxy group Aspect 24. The system of Aspect 23 further comprising a distillation apparatus connected to the filtration apparatus, and configured for collection of the stream comprising depolymerized lignin products and solvent and separation of the stream into one or more volatile streams comprising the depolymerized lignin products and a solvent stream.

Aspect 25. The system of Aspect 23 further comprising a solvent recycling apparatus connected to the distillation apparatus, and configured to receive the solvent stream recycle the solvent back to the closed cell reactor.

As used herein, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Within this specification, embodiments have been described in a way which enables a clear and concise specification to be written, but it is intended and will be appreciated that embodiments may be variously combined or separated without departing from the invention. For example, it will be appreciated that all preferred features described herein are applicable to all aspects of the invention described herein.

In some embodiments, the invention herein can be construed as excluding any element or process step that does not materially affect the basic and novel systems, and methods for depolymerizing lignin component of a lignin-containing material or using such systems. Additionally, in some embodiments, the invention can be construed as excluding any element or process step not specified herein.

EXAMPLES

Examples of the present invention will now be described. The technical scope of the present invention is not limited to the examples described below.

ABBREVIATIONS

Brewers' spent grain (BSG)
Effective carbon number (ECN)
ethyl-Guaiacol (eG)
ethyl-Syringol (eS)
Flame ionization detector (FID)
Gas chromatography (GC)
Gas chromatography with flame ionization detection (GC-FID)
Gas chromatography-mass spectrometry (GC-MS)
Municipal solid waste (MSW)
propyl-Guaiacol (pG)
propyl-Syringol (pS)
Reductive catalytic fractionation (RCF)

Materials

Materials and their source are listed below:

Biomass samples (switchgrass, poplar, MSW, were sourced from Idaho National Laboratory's Bioenergy Feedstock Library and used as received with the exception of BSG (sourced from a local brewery), technical lignins (sourced from commercial producers), and nut shells (sourced from purchased nuts). Glycerin (ACS grade), methanol (ACS grade), ethylene glycol (ACS grade), dichloromethane (stabilized, ACS grade), and cyclohexane (ACS grade), 5% Ru/C powder (Alfa Aesar), 4% Ru/Al rings (Alfa Aesar, 0.25 in. rings), 2% Ru/Al pellets (Alfa Aesar, 0.125 in. pellets), and 65% Ni/Si—Al powder (Alfa Aesar) were purchased from Fisher Scientific and used as received. Erythritol (Whole Earth Sweetener Co.) and Xylitol (NOW Foods) were purchased from Amazon.com and used as received.

Methods

Examples 1-13: Depolymerization of Lignin Component of a Lignin-Containing Material in a Reactive Distillation System 5 g of biomass or technical lignin and 75-200 mL of solvent (solvent:biomass ratio (g:mL) ranging from 40:1 to 15:1) were loaded into a 250 mL (note: this reaction has been run up to 3 L successfully) glass round bottom flask equipped with a magnetic stirbarG or mechanical stirrer. Optionally, catalyst was loaded at 50 wt % relative to the lignin component of the lignin-containing material (range 0%-200%). An open-to-atmosphere, insulated (fiberglass insulation) distillation apparatus (condenser, receiving flask) was attached. The reactor then was heated to 200-270° C., preferably 250° C., using a DrySyn block on an IKA RCT Basic hot plate with a PT1000 thermocouple placed in the DrySyn thermowell or a heating mantle equipped with a PID controller and a K-type thermocouple (submerged in the liquid). The reaction was allowed to proceed until distillate was no longer forming (approximately 4-10 hours). The distillate was collected, and the reactor was cooled to approximately 50° C. 100 mL of water or methanol was added to reduce the viscosity of the product mixture, and the reaction mixture was filtered using a Büchner funnel and Whatman Grade 4 filter paper to remove the catalyst and any solid cellulosic or lignin residue. The solids were rinsed with methanol to recover any liquid still present. The distillate was washed with dichloromethane 1-3× in a separatory funnel, and the dichloromethane layer was collected. The solvent was removed by rotary evaporation to obtain a lignin bio-oil containing predominantly substituted phenolic compounds and other substituted aromatics. The remaining liquid from the distillate contains substituted cyclopentanones, cyclopentenones, solketals, and dioxolanes. The filtrate from the bottoms optionally was washed with dichloromethane using the same procedure. Optionally, the distillate and filtrate were further extracted with a 1-6 M sodium hydroxide solution, acidified, and then extracted into a nonpolar solvent, preferably dichloromethane or ethyl acetate, to obtain higher purity phenolic/aromatic compounds. Experimental conditions and product yield are summarized in Table 1.

Examples 14-19: Depolymerization of Lignin Component of a Lignin-Containing Material in a Closed Cell System 1 g of biomass was added to 10-30 mL solvent (solvent: biomass ratio ranging from 2:1 to 30:1), typically 20 mL, in a 50 mL high-pressure Parr reactor along with 50-200 mg of catalyst (0 wt %-200 wt % relative to the lignin component of the lignin-containing material, with 50 wt % being the typical loading). The reactor was stirred with a magnetic stir barG and heated with a high-temperature heating jacket connected to a variable power supply controlled by a PID temperature controller and a K-type thermocouple to measure the reaction temperature through a thermowell. Once sealed, the reactor was purged three times with $N_2$ and then optionally pressurized with 10-40 barG of $H_2$ or $N_2$. The reactor was heated to 180-300° C. (typically 250° C.) in approximately 10-15 min and held for the designated hold time while stirring. Subsequently, the reactor was cooled in an ice bath until reaching room temperature and the gas phase was vented. A portion of the reaction products was filtered to remove solid cellulose, hemicellulose, and catalyst for further analysis. Experimental conditions and product yield are summarized in Table 1.

Product Analysis

Lignin monomer identification by gas chromatography-mass spectrometry (GC-MS). The reaction products were analyzed by GC-MS using an Agilent 7890B series GC equipped with a HP5-MS capillary column and an Agilent 5977A series mass spectrometer. The following conditions were used: injection temperature 250° C., a column temperature program of 50° C. (1 min), a ramp at 15° C./min to 300° C. and hold at 300° C. (7 min), and a detection temperature of 290° C.

tor (FID). The injection temperature was 300° C. The column temperature program was: 40° C. (3 min), ramp at a rate of 30° C./min to 100° C., then ramp at a rate of 40° C./min to 300° C., and hold at 300° C. for 5 min. The detection temperature was 300° C. The peaks in the GC-FID chromatogram appear in the same order as in a GC-MS chromatogram due to the similarities of the capillary columns. Due to the difficulty in obtaining commercially available standards, we quantified the abundance of volatile species using n-decane as an internal standard and the effective carbon number (ECN) method[1].

[1] L. Shuai, M. T. Amiri, Y. M. Questell-Santiago, F. Héroguel, Y. Li, H. Kim, R. Meilan, C. Chapple, J. Ralph and J. S. Luterbacher, *Science*, 2016, 354, 329-334.

TABLE 1

| Sample | Biomass | Lignin (%) | Catalyst | Solvent | Operating Pressure (barG) | Catalyst (wt % of lignin component) | Solvent:Biomass (vol:mass ratio) | Reaction time (hours) | Depolymerized lignin product yield (%) |
|---|---|---|---|---|---|---|---|---|---|
| 1 | Hardwood Kraft lignin (isolated) | 93 | 4% Ru/Al rings | Glycerin | 0 | 43 | 25 | 8 | 39 |
| 2 | Softwood Kraft lignin (isolated) | 93 | 4% Ru/Al rings | Glycerin | 0 | 43 | 25 | 8 | 31 |
| 3 | Soda lignin (isolated) | 100 | 5% Ru/C powder | Glycerin | 0 | 51 | 12.6 | 8 | — |
| 4 | Miscanthus | 20.4 | 5% Ru/C powder | Glycerin | 0 | 49 | 25 | 8 | 43 |
| 5 | Mixed nut shells | 40 | 5% Ru/C powder | Glycerin | 0 | 75 | 25 | 8 | 61 |
| 6 | Poplar wood | 25.7 | 5% Ru/C powder | Glycerin | 0 | 39 | 25 | 8 | — |
| 7 | Brewers' spent grain (BSG) | 3 | 2% Ru/Al pellet | Glycerin | 0 | 64 | 20 | 8 | — |
| 8 | Switchgrass | 16.2 | 5% Ru/C powder | Xylitol | 0 | 49 | 25 | 8 | 21 |
| 9 | Switchgrass | 16.2 | 5% Ru/C powder | Erythritol | 0 | 49 | 25 | 8 | 22 |
| 10 | Switchgrass | 16.2 | No catalyst | Glycerin | 0 | N/A | 25 | 8 | 36 |
| 11 | Municipal solid waste | 15 | 5% Ru/C powder | Glycerin | 0 | 50 | 25 | 8 | 51 |
| 12 | Municipal solid waste | 15 | 65% Ni/Si-Al powder | Glycerin | 0 | 50 | 25 | 8 | 61 |
| 13 | Municipal solid waste | 15 | No catalyst | Glycerin | 0 | N/A | 25 | 8 | 52 |
| 14 | Poplar wood | 26 | 5% Ru/C powder | Ethylene glycol, 200° C. | 2-5 | 38 | 20 | 3 | — |
| 15 | Poplar wood | 26 | 5% Ru/C powder | Ethylene glycol, 250° C. | 5-10 | 38 | 20 | 3 | — |
| 16 | Poplar wood | 26 | 5% Ru/C powder | Glycerin | 5 | 38 | 20 | 15 | — |
| 17 | Poplar wood | 26 | 5% Ru/C powder | Glycerin | 40 (40 barG external $H_2$) | 38 | 20 | 15 | — |
| 18 | Poplar wood | 26 | 5% Ru/C powder | Methanol | 120 (40 barG external $H_2$) | 38 | 20 | 15 | 51 |
| 19 | Poplar wood | 26 | 5% Ru/C powder | Methanol | 80 | 38 | 20 | 20 | 41 |

Figure 3:
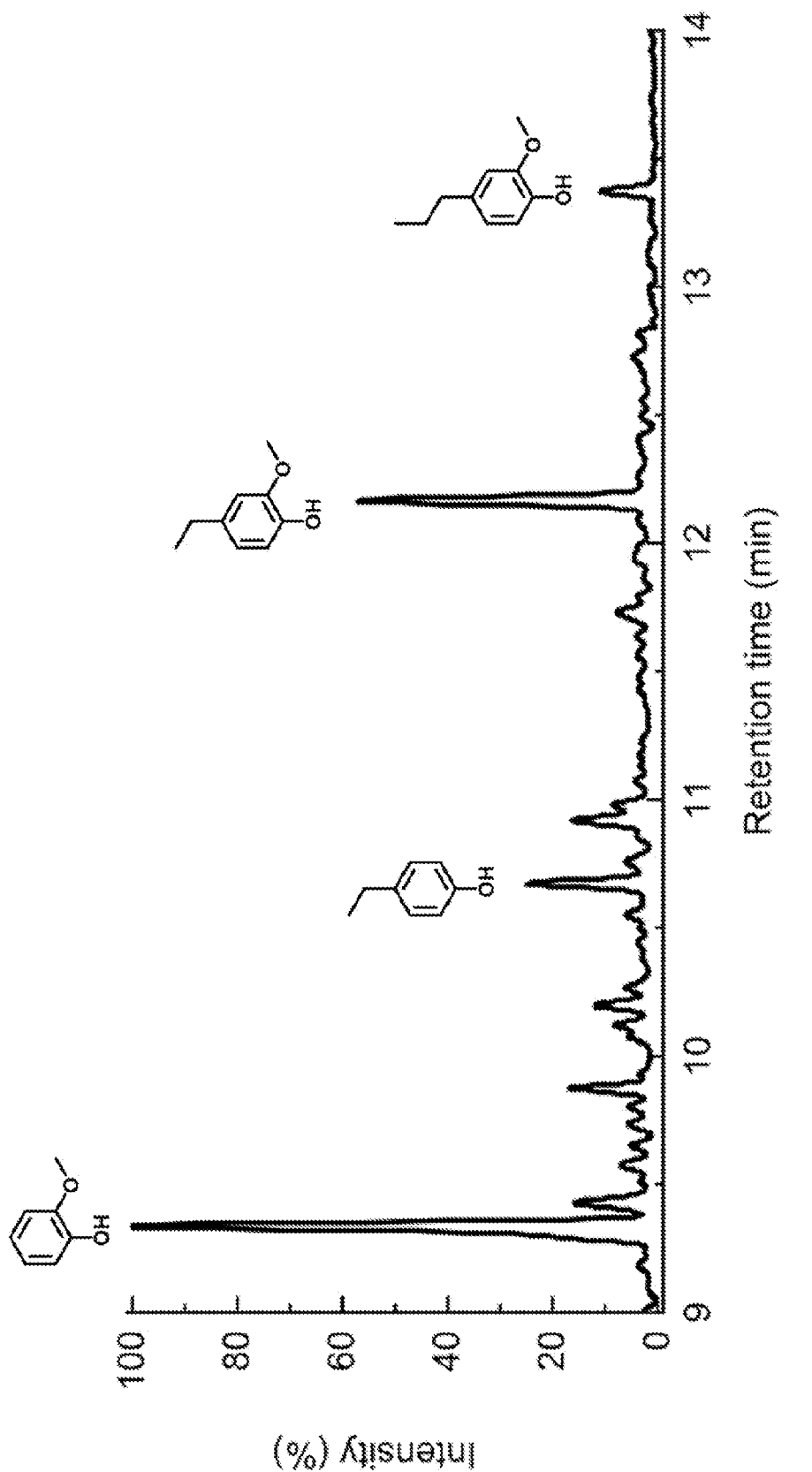
FIG. 3 shows an exemplary gas chromatography (GC) trace of depolymerized lignin products from softwood Kraft lignin with no added hydrogen in a reactive distillation system (2.5 g Ru/Al, 125 mL glycerin, 250° C., 8 h, ambient pressure), after extraction with dichloromethane, according to embodiments of the present invention.

*The masses of different Ru catalysts were normalized on a Ru weight basis to the 5% Ru/C powder (e.g., 1 g of 2% Ru/Al pellets is equivalent to 0.4 g of 5% Ru/C powder)
**Operating temperature was 250° C. unless specified
***No external gas ($H_2$ or $N_2$) was added unless specified. For closed systems, the headspace was flushed with nitrogen $N_2$ but not pressurized prior to sealing the reactor.
"—" indicates phenolic products were detected by GC-MS but yield was not quantified
Entries 1-13 are reactive distillations; entries 14-17 are closed systems Lignin monomer quantification by gas chromatography with flame ionization detection (GC-FID). The reaction products were analyzed with a GC (Agilent 7890B series) equipped with an HP5-column and a flame ionization detec- As summarized in Table 1, Example Nos. 1-3 show that the inventive process using a reactive distillation system can be successfully applied to various isolated/technical lignins. In particular, FIG. 3 shows an exemplary gas chromatography (GC) trace of depolymerized lignin products obtained from softwood Kraft lignin, as summarized in Example No. 2 in Table 1, with no added hydrogen in a reactive distillation system (2.5 g Ru/Al, 125 mL glycerin, 250° C., 8 h, ambient pressure), after extraction with dichloromethane, according to embodiments of the present invention. As can be seen from FIG. 3, the depolymerized lignin products included, guaiacol, eG, pG, and ethyl phenol.

As summarized in Table 1, Example Nos. 4-7 show that the inventive process using a reactive distillation system can be successfully applied to a variety of lignin-containing lignocellulosic biomass and pretreated lignocellulosic biomass. These examples show that the present invention is applicable to untreated lignocellulosic biomasses from grasses, woods, food residues, and partially extracted lignocellulosic biomass.

Figure 4A:
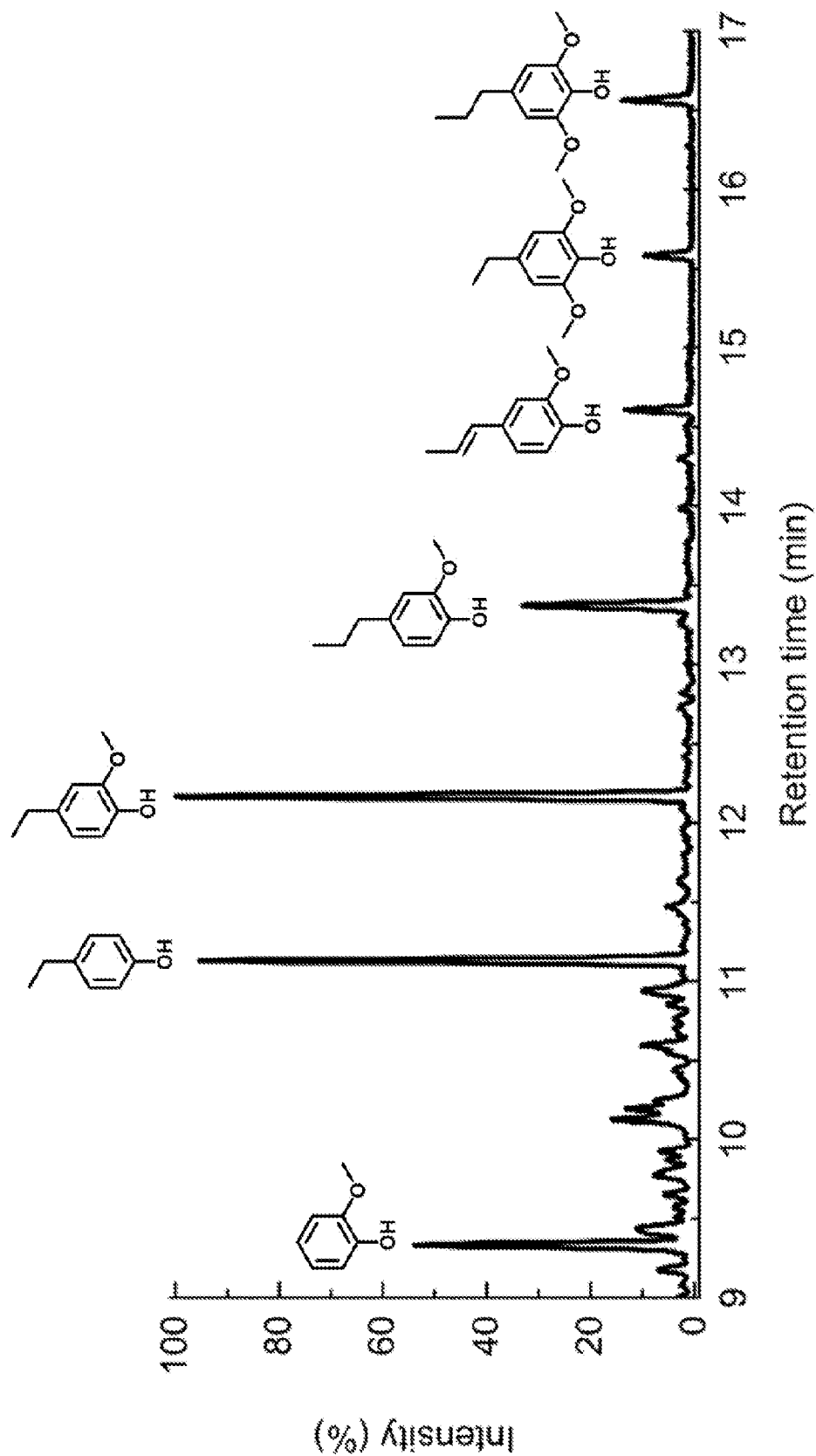
FIG. 4A shows an exemplary gas chromatography (GC) trace of depolymerized lignin products from switchgrass with no added hydrogen in a reactive distillation system (0.4 g Ru/Al, 125 mL erythritol, 250° C., 8 h, ambient pressure), after extraction with dichloromethane, according to embodiments of the present invention.
Figure 4B:
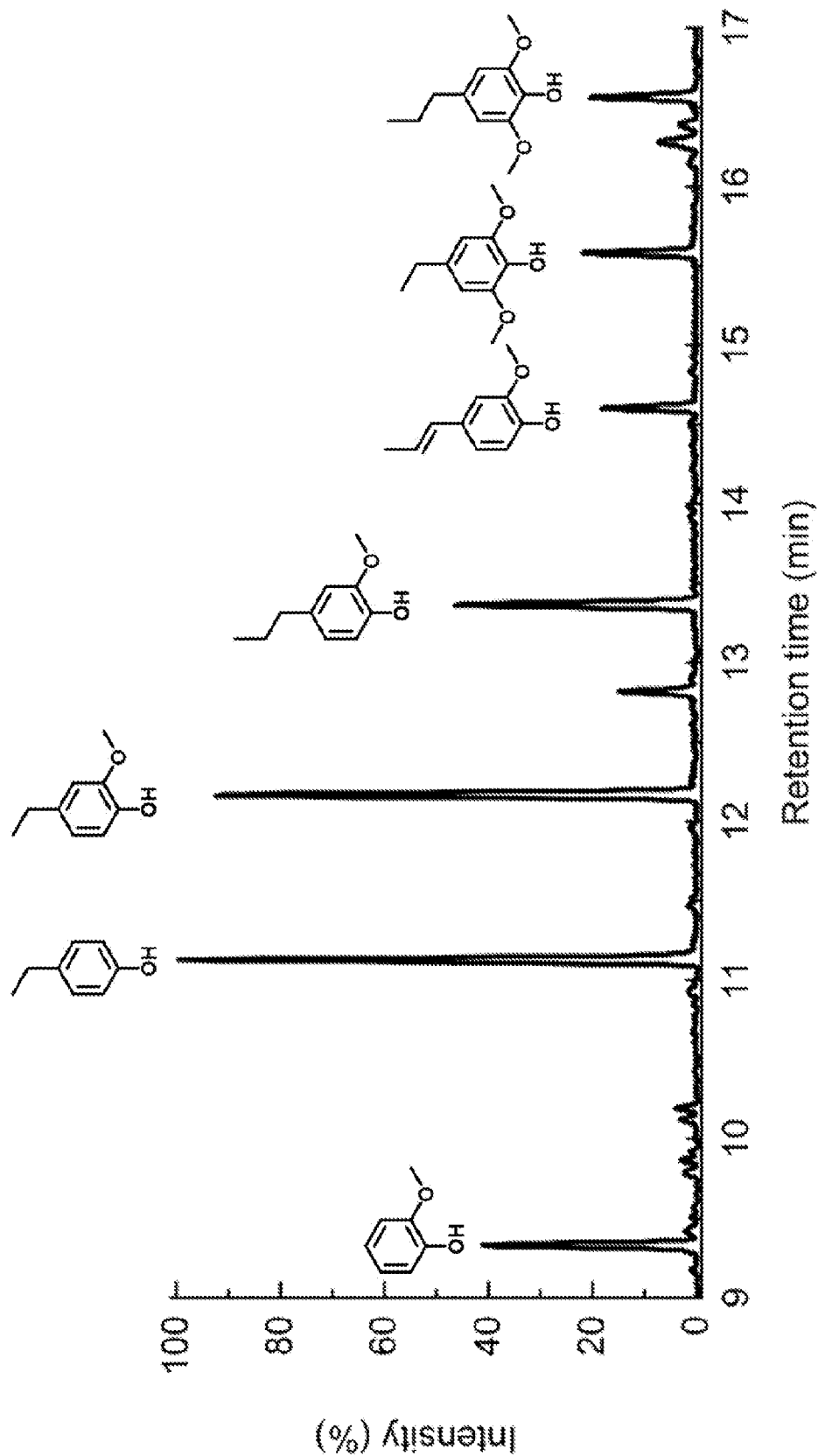
FIG. 4B shows an exemplary gas chromatography (GC) trace of depolymerized lignin products from switchgrass with no added hydrogen in a reactive distillation system (0.4 g Ru/Al, 125 mL xylitol, 250° C., 8 h, ambient pressure), after extraction with dichloromethane, according to embodiments of the present invention.

FIGS. 4A and 4B show exemplary gas chromatography (GC) traces of depolymerized lignin products from switchgrass, as summarized in Examples 8-9 in Table 1, with no added hydrogen, in a reactive distillation system (0.4 g Ru/Al, 125 mL erythritol or xylitol, 250° C., 8 h, ambient pressure), after extraction with dichloromethane, according to embodiments of the present invention. Example No. 10 (no catalyst, 125 mL glycerin, 250° C., 8 h, ambient pressure) is the same as Example Nos. 8-9 except no catalyst was added. These Examples show that depolymerization according to the inventive method can be carried out in a variety of solvents, including unconventional protic solvents, with or without a metal catalyst and without hydrogen or harsh solvent such as methanol.

Figure 5:
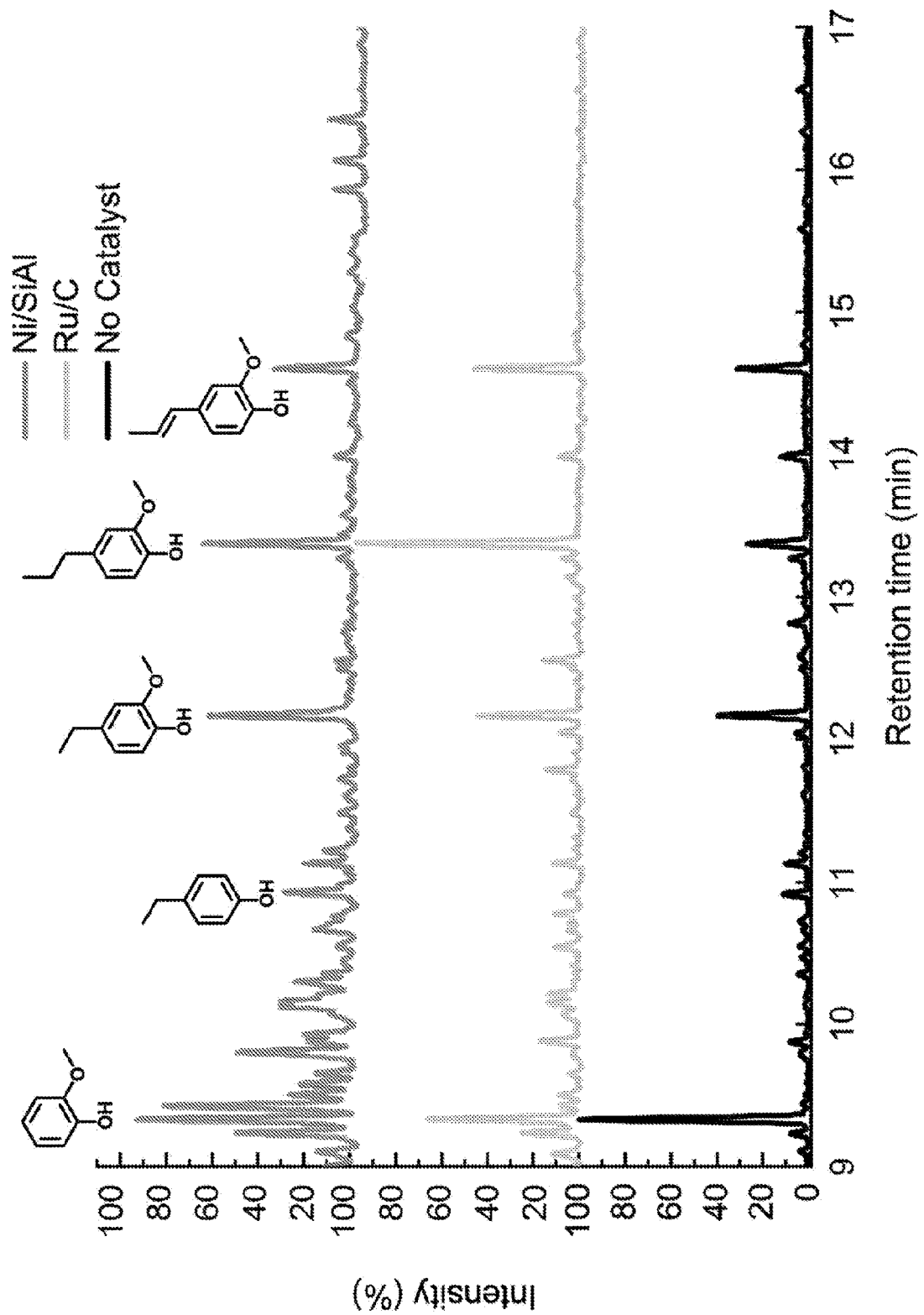
FIG. 5 shows exemplary gas chromatography (GC) traces of depolymerized lignin products from municipal solid waste with no added hydrogen in a reactive distillation system with Ru/C (solid line), Ni/SiAl (dashed line), and no catalyst (dotted line), (5 g MSW, 0.4 g Ru/C or Ni/SiAl, 125 mL glycerin, 250° C., 8 h, ambient pressure), after extraction with dichloromethane, according to embodiments of the present invention.

FIG. 5 shows exemplary gas chromatography (GC) traces of depolymerized lignin products from municipal solid waste, as summarized in Examples 11-13 in Table 1, with no added hydrogen, in a reactive distillation system with Ru/C (solid line), Ni/SiAl (dashed line), and no catalyst (dotted line), (5 g MSW, 0.4 g Ru/C or Ni/SiAl, 125 mL glycerin, 250° C., 8 h, ambient pressure), after extraction with dichloromethane, according to embodiments of the present invention. These examples show the robustness of the inventive process, that the process is applicable to extremely heterogeneous feedstocks and with or without catalyst. Additionally, these examples show that a variety of hydrogenation catalysts (e.g., Ni- or Ru-based catalysts) can be used to carry out this process.

Figure 6A:
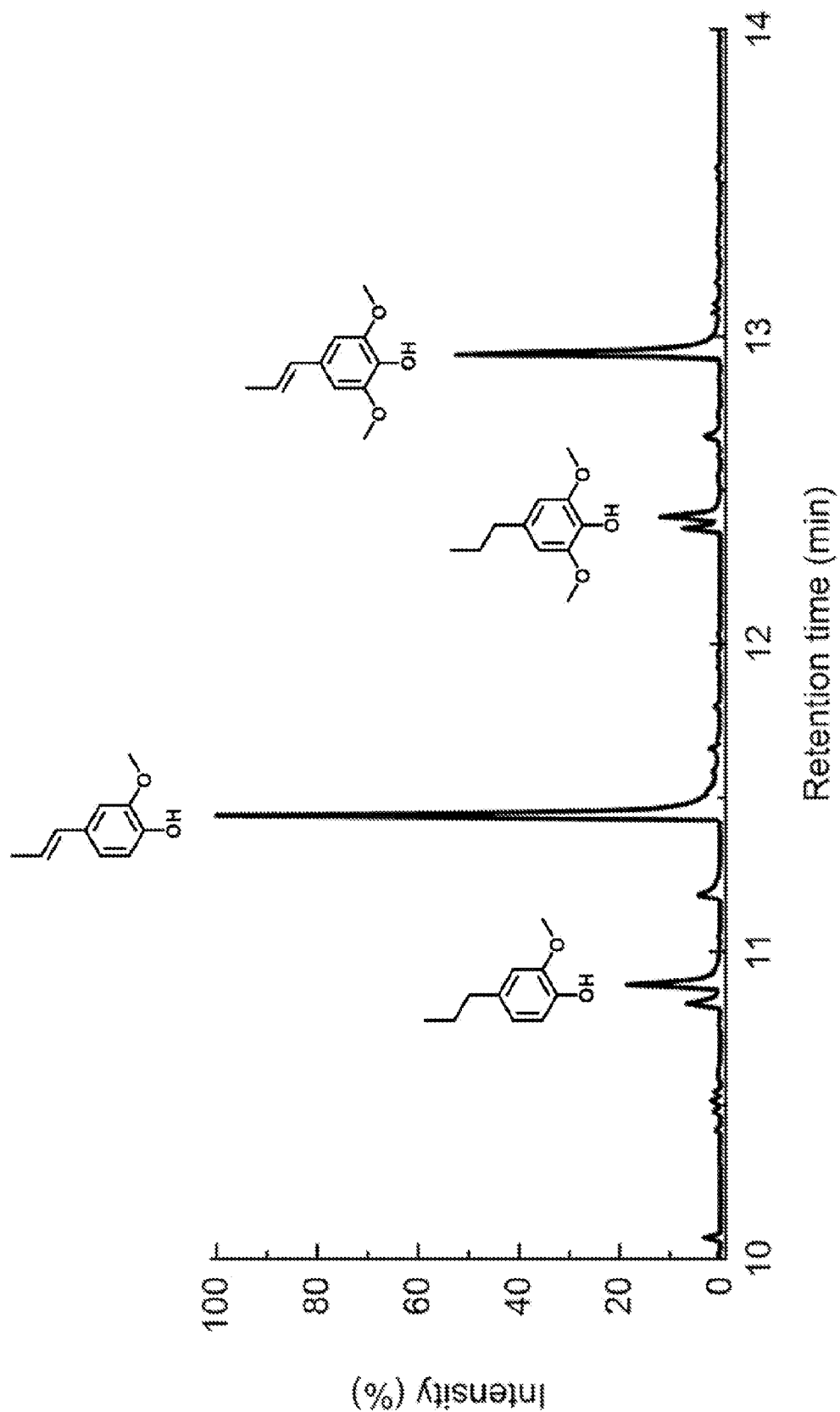
FIG. 6A shows an exemplary gas chromatography (GC) trace of depolymerized lignin products of poplar wood with no added hydrogen in a closed system (0.1 g Ru/C, 20 mL ethylene glycol, 200° C., 3 h, operating pressure~2-5 barG), after extraction with cyclohexane, according to embodiments of the present invention.
Figure 6B:
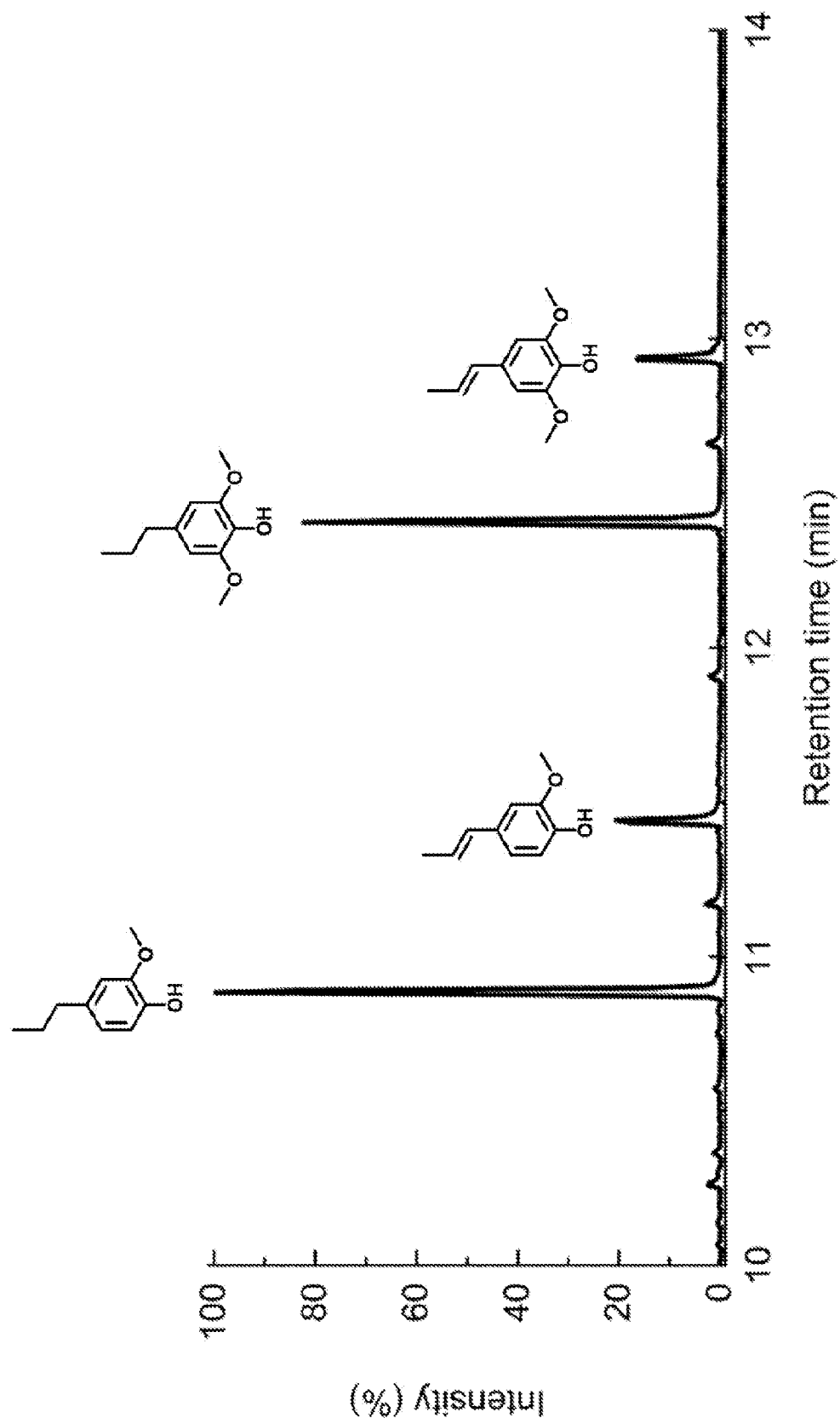
FIG. 6B shows an exemplary gas chromatography (GC) trace of depolymerized lignin products of poplar wood with 40 barG of hydrogen in a closed system (0.1 g Ru/C, 20 mL ethylene glycol, 250° C., 3 h, operating pressure 5-10 barG), after extraction with cyclohexane, according to embodiments of the present invention.

FIGS. 6A and 6B show exemplary gas chromatography (GC) traces of depolymerized lignin products of poplar wood, with no added hydrogen, in a closed system, as summarized in Example Nos. 14-15 in Table 1, (0.1 g Ru/C, 20 mL ethylene glycol, 200° C. and 250° C., 3 h, operating pressure of 2-5 barG and 5-10 barG respectively), after extraction with cyclohexane, according to embodiments of the present invention. Comparison of GC trace of Example No. 14 (FIG. 6A) with that of No. 15 (FIG. 6B) show that higher temperatures shift the product distribution towards saturated compounds, e.g. propylguaiacol versus isoeugenol.

Figure 7A:
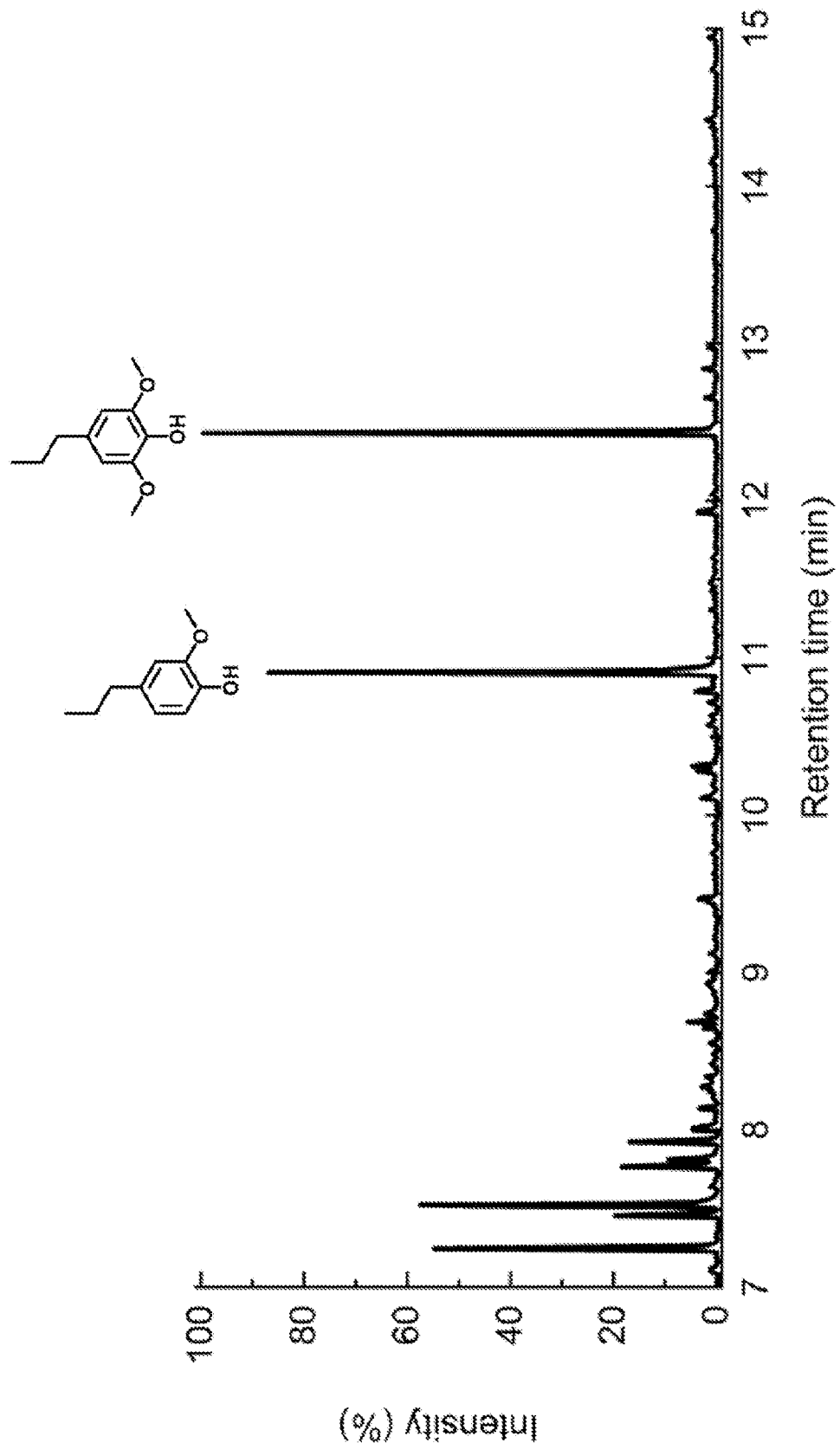
FIG. 7A shows an exemplary gas chromatography (GC) trace of depolymerized lignin products of poplar wood with no added hydrogen in a closed system (0.1 g Ru/C, 20 mL glycerin, 250° C., 15 h, operating pressure~5 barG), after extraction with cyclohexane, according to embodiments of the present invention.
Figure 7B:
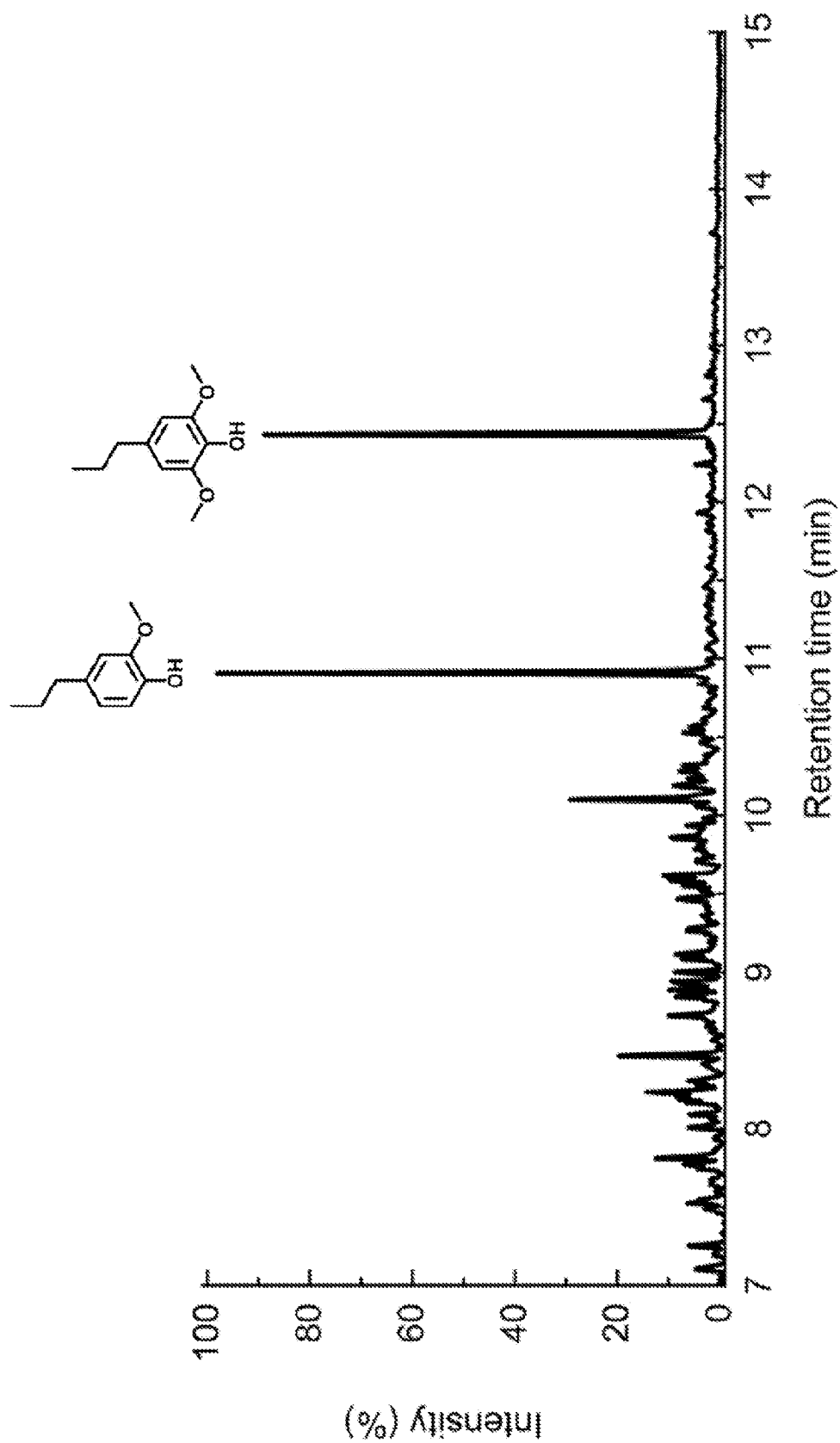
FIG. 7B shows an exemplary gas chromatography (GC) trace of depolymerized lignin products of poplar wood with 40 barG of hydrogen in a closed system (0.1 g Ru/C, 20 mL glycerin, 250° C., 15 h, operating pressure~40 barG), after extraction with cyclohexane, according to embodiments of the present invention.

FIGS. 7A and 7B show exemplary gas chromatography (GC) traces of depolymerized lignin products of poplar wood, with no added hydrogen and added hydrogen, in a closed system, as summarized in Example Nos. 16 and 17 respectively in Table 1 (0.1 g Ru/C, 20 mL glycerin, 250° C., 15 h, operating pressure ~5 barG and 40 barG (with 40 barG of external $H_2$) respectively), after extraction with cyclohexane, according to embodiments of the present invention. This clearly shows that the inventive process is successful in glycerin with and without hydrogen in a closed system and can be performed while maintaining operating pressures below 10 barG.

Figure 8A:
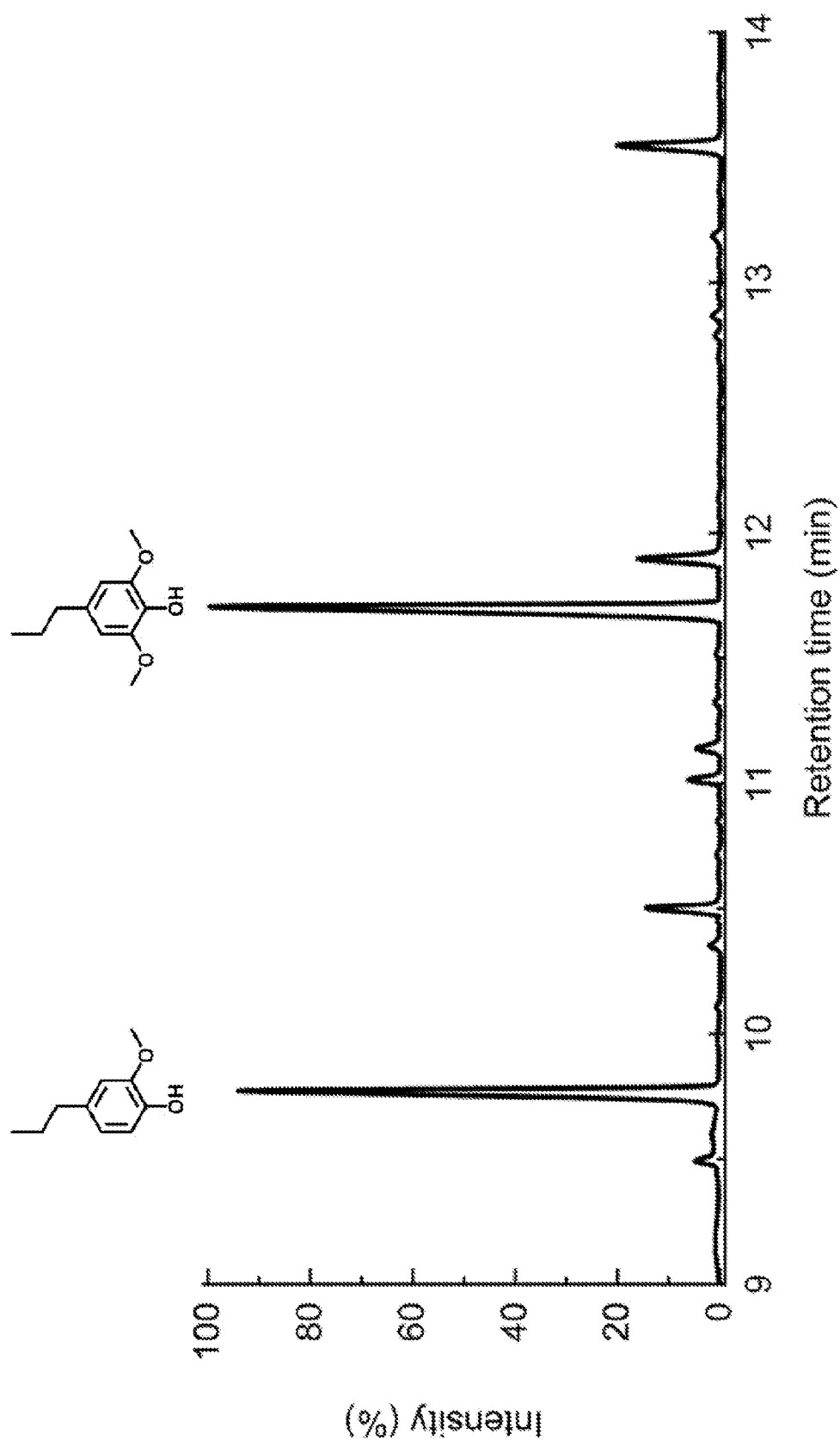
FIG. 8A shows an exemplary gas chromatography (GC) trace of depolymerized lignin products of poplar wood with no added hydrogen and added hydrogen in a closed system (0.1 g Ru/C, 20 mL methanol, 250° C., 15 h, operating pressure~80 barG), after extraction with cyclohexane, according to embodiments of the present invention.
Figure 8B:
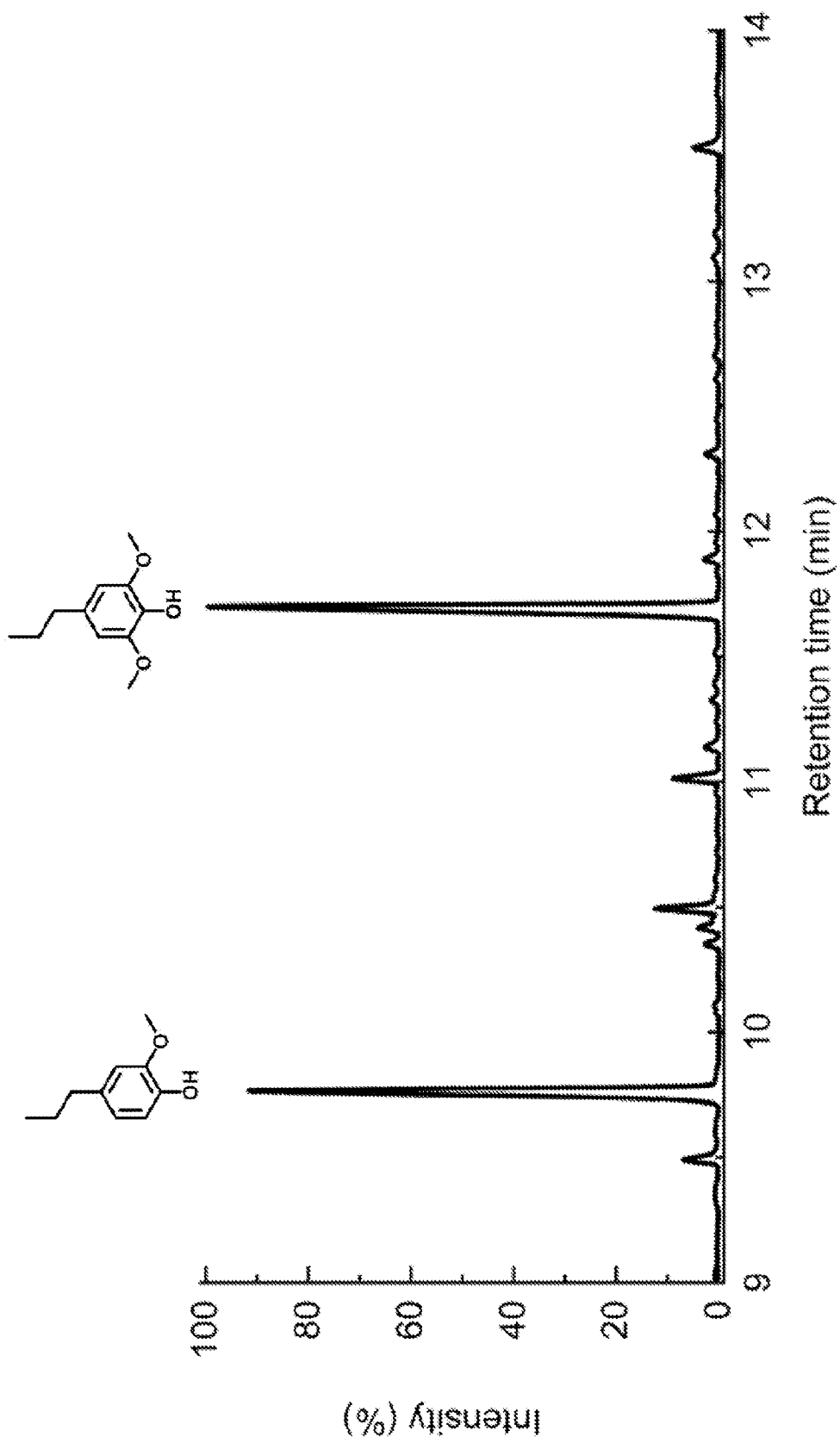
FIG. 8B shows an exemplary gas chromatography (GC) trace of depolymerized lignin products of poplar wood with added hydrogen in a closed system (0.1 g Ru/C, 20 mL methanol, 250° C., 15 h, operating pressure~120 barG (with 40 barG $H_2$)), after extraction with cyclohexane, according to embodiments of the present invention.

FIGS. 8A, and 8B show exemplary gas chromatography (GC) traces of depolymerized lignin products of poplar wood, with no added hydrogen and added hydrogen, in a closed system, as summarized in Example Nos. 19 and 18 respectively in Table 1 (0.1 g Ru/C, 20 mL methanol, 250° C., 15 h, operating pressure ~80 barG or 120 barG (with $H_2$)), after extraction with cyclohexane. This serves as a comparative example to highlight the significantly reduced pressure from the invention in comparison to conventional methods to depolymerize lignin.

Figure 8C:
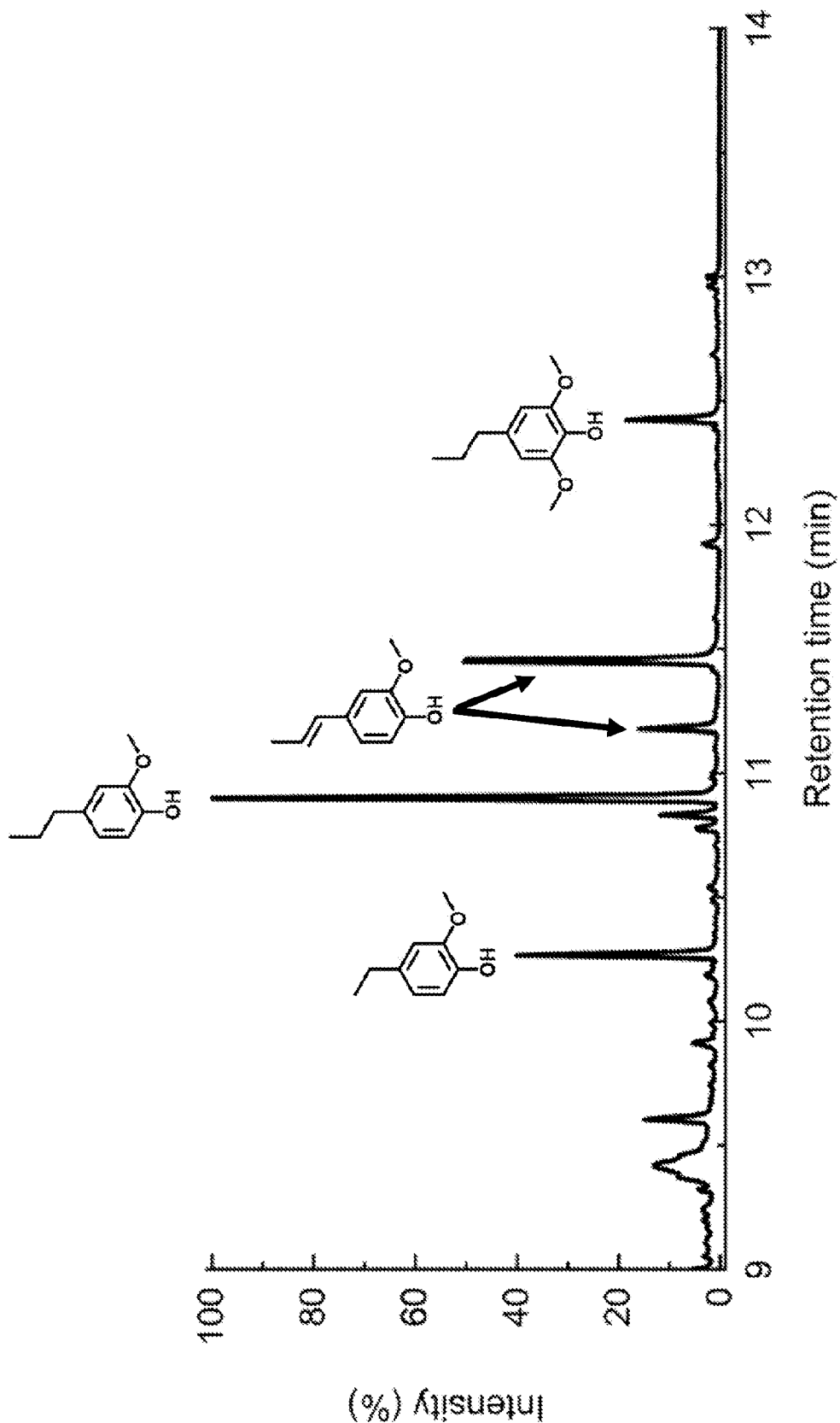
FIG. 8C shows an exemplary gas chromatography (GC) trace of depolymerized lignin products of poplar wood in a reactive distillation system (0.1 g Ru/C, 20 mL glycerin, 250° C., 6 h, ambient pressure), after extraction with cyclohexane, according to embodiments of the present invention.

FIG. 8C shows an exemplary gas chromatography (GC) trace of depolymerized lignin products of poplar wood in a reactive distillation system (0.1 g Ru/C, 25 mL glycerin, 250° C., 6 h, ambient pressure), after extraction with cyclohexane, according to embodiments of the present invention.

Comparison of FIGS. 8A and 8B with FIG. 8C show that the lignin depolymerization can be carried out safely using less toxic chemicals (glycerin versus methanol), at ambient pressure as compared to high pressures, and with no added hydrogen, thereby reducing overall cost of manufacturing and at the same time with improved safety.

Thus, the above Examples show the robustness of the inventive processes of the present invention, and in particular, that the process is applicable to a wide range of lignin containing lignocellulosic biomass, catalysts, solvents, pressure, and hydrogen content.

The invention claimed is:

1. A method of depolymerizing a lignin component of a lignin-containing material comprising:
   (i) contacting the lignin-containing material with a solvent and optionally a catalyst at a temperature in the range of 180-300° C. and at a maximum operating pressure of less than 10 barG during the depolymerization of the lignin component of the material, wherein the solvent has a boiling point higher than the reaction temperature; and
   (ii) collecting at least one volatile stream comprising one or more depolymerized lignin products, wherein at least one of the one or more depolymerized lignin products comprises a substituted phenol having the following general formula:

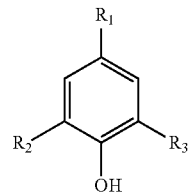

wherein $R_1$ is H, methyl, ethyl, n-propyl, propenyl, or allyl, and $R_2$ and $R_3$ are independently selected from H or methoxy group, and
   wherein the step of contacting the lignin-containing material with the solvent and optionally the catalyst is carried out in a reactive distillation reactor, and
   wherein the step of collecting at least one volatile stream comprises concurrently collecting at least one volatile stream via a distillation apparatus connected to the reactive distillation reactor.

2. The method according to claim 1, wherein the step of contacting the lignin-containing material with the solvent and optionally the catalyst comprises contacting in the presence of a hydrogenolysis catalyst.

3. The method according to claim 2, wherein the catalyst comprises Ru, Ni, Raney Ni, Pd, NiPd, NiCu, NiCo, NiRu, RuPd, Fe, Co, Pt, Cu, or mixtures thereof.

4. The method according to claim 3, wherein the catalyst is supported on a support selected from the group consisting of carbon, alumina, silica, and alumina-silica.

5. The method according to claim 2, wherein a mass % of catalyst relative to the lignin component of the lignin-containing material is in a range of 0% to 200%.

6. The method according to claim 1, wherein the solvent is a protic solvent selected from the group consisting of ethylene glycol, glycerin, erythritol, threitol, xylitol, arabitol, ribitol, mannitol, sorbitol, galactitol, fucitol, iditol, inositol, volemitol, monosaccharides, and mixtures thereof.

7. The method according to claim 1, wherein the step of contacting the lignin-containing material with the solvent and optionally the catalyst comprises contacting in the presence of nitrogen, air or argon, without added hydrogen.

8. The method according to claim 1, wherein the step of contacting the lignin-containing material with the solvent and optionally the catalyst comprises contacting in the presence of hydrogen at a maximum operating pressure of less than 10 barG.

9. The method according to claim 1, wherein the step of collecting at least one volatile stream further comprises extracting one or more depolymerized lignin products from at least one of the collected volatile streams by one of distillation, liquid-liquid extraction, chromatography, or extraction by a base followed by acidification.

10. The method according to claim 1, wherein the volatile depolymerized lignin products comprise 2-methoxy-4-propylphenol, 2-methoxy-4-ethylphenol, 2-methoxyphenol, 2,6-dimethoxy-4-propylphenol, 2,6-dimethoxy-4-ethylphenol, 2,6-dimethoxyphenol, or mixtures thereof.

11. The method according to claim 1, wherein at least one volatile stream comprises one or more non-phenolic compounds.

12. The method according to claim 11, wherein the non-phenolic compounds comprise substituted furans, substituted methoxybenzenes, substituted cyclopentanones, substituted cyclopentenones, dioxalanes, solketal, and mixtures thereof.

13. The method according to claim 1, wherein the lignin-containing material comprises untreated lignocellulosic biomass selected from woods, grasses, cereal crops and waste; partially treated lignocellulosic biomass, an isolated lignin, or mixtures thereof.

14. The method according to claim 1, wherein the lignin-containing material comprises oak, alder, chestnut, ash, aspen, balsa, beech, birch, boxwood, walnut, laurel, camphor, chestnut, cherry, dogwood, elm, *eucalyptus*, pear, hickory, ironwood, maple, olive, poplar, *sassafras*, rosewood, coconut, locust, willow trees, *miscanthus*, switchgrass, bamboo, straw, barley, millet, wheat, corn stover, sugarcane bagasse, nutshells, olive seeds, tomato peels, brewers' spent grain (BSG), seeds, lignin-containing yard waste, lignin-containing municipal solid waste, lignin residue generated by cellulosic biorefinery and paper pulping industries, and mixtures thereof.

15. The method according to claim 1, wherein the step of contacting the lignin-containing material with the solvent comprises contacting the lignin-containing material with the catalyst in the reactive distillation reactor, and
wherein the step of collecting at least one volatile stream comprises concurrently collecting at least one volatile stream via distillation apparatus connected to the reactive distillation reactor.

16. The method according to claim 1, wherein the step of contacting the lignin-containing material with a solvent and optionally a catalyst is carried out in a closed cell reactor, and
wherein the subsequent step of collecting at least one volatile stream comprises collecting at least one volatile stream via distillation apparatus connected to the closed cell reactor, after the step of contacting the lignin-containing material with a solvent and optionally a catalyst.

17. The method of claim 1 comprising:
(i) providing a composition comprising one or more of the depolymerized lignin products collected at least one volatile stream, a solvent, and optionally one or more of the of partially depolymerized lignin, residual cellulose/hemicellulose and other non-lignin feedstock components, wherein the solvent has lower volatility than one or more of the depolymerized lignin products collected at least one volatile stream; and
(ii) distilling one or more depolymerized lignin products collected at least one volatile stream from the composition, wherein at least one of the one or more depolymerized lignin products collected at least one volatile stream comprises a substituted phenol having the following general formula:

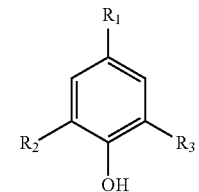

wherein $R_1$ is H, methyl, ethyl, n-propyl, propenyl, allyl, or formyl, and $R_2$ and $R_3$ are independently selected from H or methoxy group.

18. The method of claim 17, wherein the solvent is selected from the group consisting of ethylene glycol, glycerin, erythritol, threitol, xylitol, arabitol, ribitol, mannitol, sorbitol, galactitol, fucitol, iditol, inositol, volemitol, monosaccharides, and mixtures thereof.

* * * * *

UNITED STATES PATENT AND TRADEMARK OFFICE
CERTIFICATE OF CORRECTION

| | | |
|---|---|---|
| PATENT NO. | : 12,358,858 B2 | Page 1 of 1 |
| APPLICATION NO. | : 17/634271 | |
| DATED | : July 15, 2025 | |
| INVENTOR(S) | : Elvis O. Ebikade et al. | |

It is certified that error appears in the above-identified patent and that said Letters Patent is hereby corrected as shown below:

In the Claims

In Column 23, Claim 12, Line 43, delete "dioxalanes" and insert -- dioxolanes --

In Column 24, Claim 17, Line 25, the phrase "providing a composition comprising one or more of the depolymerized lignin products collected at least one volatile stream, a solvent, and optionally" should read -- providing a composition comprising one or more of the depolymerized lignin products of the collected at least one volatile stream, a solvent, and optionally --

In Column 24, Claim 17, Line 27, delete "the of" and insert -- the --

Signed and Sealed this
Eighteenth Day of November, 2025

John A. Squires
*Director of the United States Patent and Trademark Office*